(12) United States Patent
Woltermann

(10) Patent No.: US 11,911,603 B2
(45) Date of Patent: Feb. 27, 2024

(54) ELECTRICAL MUSCLE STIMULATION (EMS) SUIT WITH ELECTRODE ARRANGEMENT THAT PREVENTS TRANSTHORACIC ELECTRICAL CURRENT

(71) Applicant: Katalyst Interactive Inc., Tumwater, WA (US)

(72) Inventor: Björn Erich Woltermann, Seattle, WA (US)

(73) Assignee: KATALYST INTERACTIVE INC., Tumwater, WA (US)

( * ) Notice: Subject to any disclaimer, the term of this patent is extended or adjusted under 35 U.S.C. 154(b) by 151 days.

(21) Appl. No.: 16/735,529

(22) Filed: Jan. 6, 2020

(65) Prior Publication Data

US 2021/0205605 A1 Jul. 8, 2021

(51) Int. Cl.
*A61N 1/04* (2006.01)

(52) U.S. Cl.
CPC ......... *A61N 1/0452* (2013.01); *A61N 1/0484* (2013.01)

(58) Field of Classification Search
CPC ................ A61N 1/0452; A61N 1/0484; A61N 1/36003; A61N 1/3603
USPC .......................................................... 607/48
See application file for complete search history.

(56) References Cited

U.S. PATENT DOCUMENTS

| | | |
|---|---|---|
| D321,761 S | 11/1991 | Shimizu |
| D796,681 S | 9/2017 | Seval et al. |
| D846,133 S | 4/2019 | Matsushita |
| D847,358 S | 4/2019 | Matsushita |
| D870,299 S | 12/2019 | Lin |
| D879,306 S | 3/2020 | Frouin |
| D898,202 S | 10/2020 | Vosch et al. |
| D907,213 S | 1/2021 | Vosch et al. |
| D907,783 S | 1/2021 | Cole |
| D918,393 S | 5/2021 | Geissen |
| 2012/0245483 A1* | 9/2012 | Lundqvist .............. A61B 5/296 600/546 |
| 2018/0028810 A1* | 2/2018 | Schwarz ............... A61N 1/0452 |
| 2018/0036531 A1* | 2/2018 | Schwarz ................ G16H 20/30 |
| 2018/0311492 A1 | 11/2018 | Matsushita |
| 2018/0325452 A1* | 11/2018 | Woltermann ........ A61N 1/0476 |

(Continued)

OTHER PUBLICATIONS 008429328-001.

(Continued)

*Primary Examiner* — Carl H Layno
*Assistant Examiner* — Jane C Kalinock
(74) *Attorney, Agent, or Firm* — Lee & Hayes P.C.

(57) ABSTRACT

An electrical muscle stimulation (EMS) suit having electrodes affixed thereto is disclosed. The EMS suit may include a vest portion comprising a left front portion, a right front portion, and a back portion, as well as a processor and memory storing pulse parameter settings. In some embodiments, the left front portion has a first pair of electrodes on a first channel, and the right front portion has a second pair of electrodes on a second channel. In some embodiments, the back portion has a third pair of electrodes on a third channel and positioned in a left half of the back portion, as well as a fourth pair of electrodes on a fourth channel and positioned in a left half of the back portion. During operation of the EMS suit, electrical impulses are delivered via the pairs of electrodes in accordance with the pulse parameter settings to elicit muscle contraction.

8 Claims, 9 Drawing Sheets

(56) References Cited

U.S. PATENT DOCUMENTS

| | | | |
|---|---|---|---|
| 2020/0061366 A1* | 2/2020 | Decker | A61N 1/0492 |
| 2020/0353239 A1* | 11/2020 | Daniels | A61N 1/02 |
| 2021/0038155 A1 | 2/2021 | Kim | |
| 2021/0154571 A1* | 5/2021 | Fuertes Pena | A61N 1/0484 |

OTHER PUBLICATIONS

Chinese Office Action dated Mar. 10, 2021 for Chinese Design Application No. 202030359281.6, a counterpart foreign application of U.S. Appl. No. 29/719,615, 1 page.

Chinese Office Action dated Dec. 17, 2020 for Chinese Design Application No. 202030359281.6, a counterpart foreign application of U.S. Appl. No. 29/719,615, 1 page.

D2017-4852.

Electric Vest—One 4x10 Dual Electrode included, retrieved Jun. 2021 at <<https://www.mmarmmedical.com/Electric-Vest-Garment-One-4-x-10-Dual-Electrode-p/ev1-410.htm>>, 1 pg.

Office Action for U.S. Appl. No. 29/719,615, dated Jun. 28, 2021, Woltermann, "Electrodes of an Electrical Muscle Stimulation (EMS) Suit ", 10 Pages.

* cited by examiner

ELECTRICAL MUSCLE STIMULATION (EMS) SUIT WITH ELECTRODE ARRANGEMENT THAT PREVENTS TRANSTHORACIC ELECTRICAL CURRENT

BACKGROUND

Electrical Muscle Stimulation (EMS) is a technology that elicits muscle contraction using electrical impulses. The impulses are delivered via electrodes placed on the body near the muscles that are to be stimulated. EMS technology has been used to develop fitness products, such as EMS suits, which are designed to help users achieve their health and fitness goals, whether the goal is to increase muscle activation, improve muscle tone, increase strength, and/or recover from an injury. When a user wears an EMS suit, the electrodes in the suit are situated near particular muscles groups (e.g., arms, legs, chest, abdominals, back, etc.) in order to deliver electrical impulses targeted to those muscle groups while the user performs various exercise movements. If careful precautions are not taken regarding the arrangement of the electrodes on the EMS suit and/or the parameters of the electrical impulses (e.g., intensity, pulse width, etc.), it is possible to design an EMS suit that is unsafe to use, at least for a subset of the general population who may be at high risk for certain medical conditions, like heart failure.

Discussed herein are technological improvements for, among other things, these devices and systems.

BRIEF DESCRIPTION OF THE DRAWINGS

The detailed description is described with reference to the accompanying figures. In the figures, the left-most digit(s) of a reference number identifies the figure in which the reference number first appears. The same reference numbers in different figures indicate similar or identical items.

DETAILED DESCRIPTION

Figure 1:
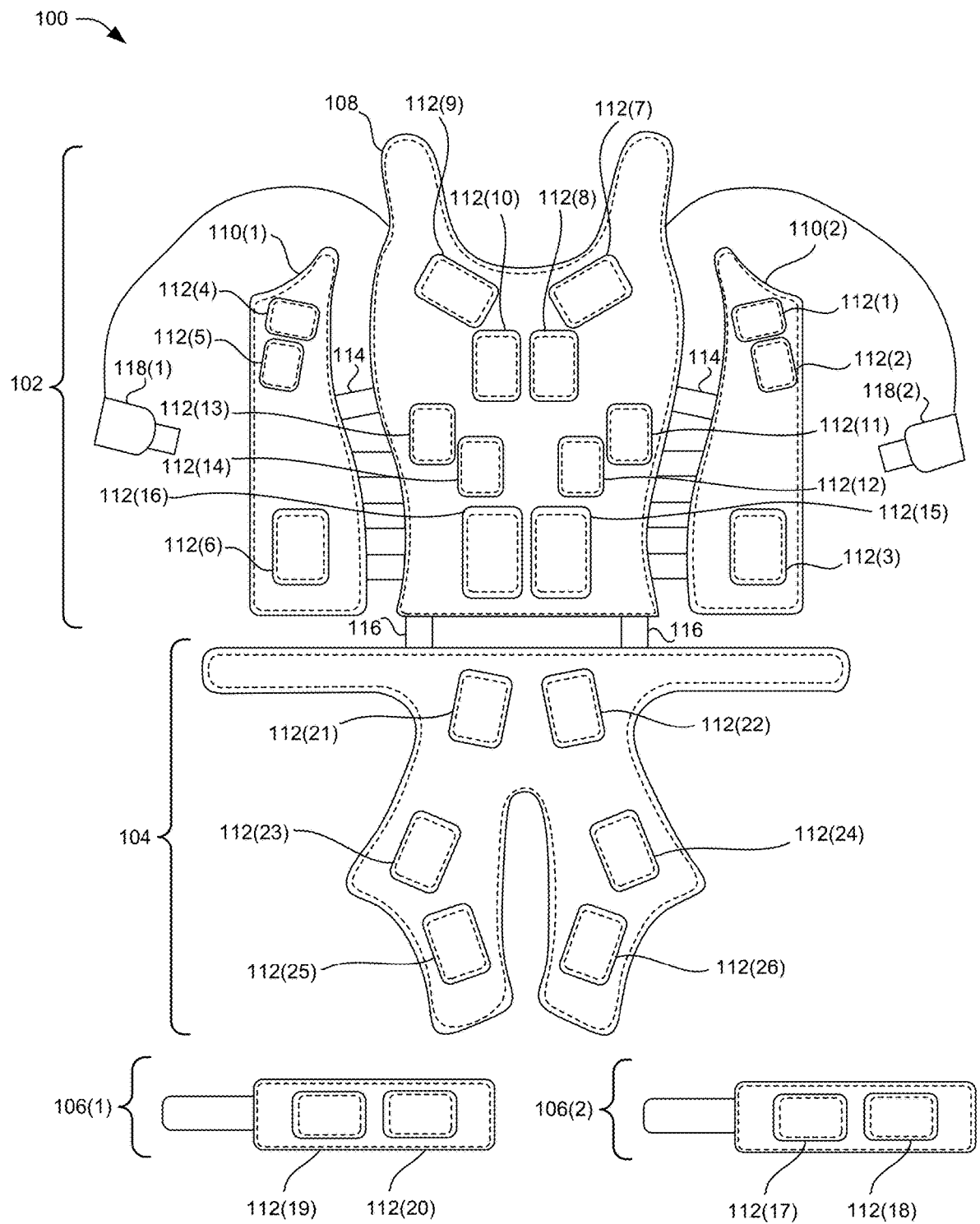
FIG. 1 is a schematic diagram of an illustrative EMS suit having an arrangement of electrodes that prevents transthoracic electrical current, according to embodiments described herein.

This disclosure is directed to, among other things, an electrical muscle stimulation (EMS) suit having electrodes affixed thereto, wherein the electrodes are positioned on the EMS suit in an arrangement that prevents transthoracic flow of electrical current through a body of a user wearing the EMS suit during operation of the EMS suit. Individual electrodes of the EMS suit are controllable by a processor(s) to deliver electrical impulses to muscles of a user who is wearing the EMS suit. When an electrical impulse is delivered via a pair of electrodes, electrical current (i.e., the flow of charged particles) flows from one electrode (of the pair), through a portion of the user's body (e.g., through muscle tissue underlying the pair of electrodes), and to the other electrode (of the pair). The user's body completes an electrical circuit that includes the pair of electrodes, thereby allowing electrical current to flow between the pair of electrodes during operation of the EMS suit, as electrical impulses are delivered via the electrodes. As used herein, a "pair" of electrodes can mean two electrodes that correspond to a common channel of multiple channels that are used to deliver electrical impulses, channel-by-channel, during operation of the EMS suit. A "pair" of electrodes can also mean two electrodes that allow for electrical current to flow therebetween during operation of the EMS suit, one electrode of the pair operating as a positive electrode (anode) and the other electrode of the pair operating as a negative electrode (cathode). It is to be appreciated that, with alternating current (AC), each electrode of a given pair reverses current with each cycle (or frame). That is, each electrode may change from a positive electrode (anode) to a negative electrode (cathode) with each cycle (or frame).

In general, the electrodes of the EMS suit are arranged in the EMS suit to cover parts of the user's body in order to excite particular muscle groups (e.g., arms, legs, chest, abdominals, back, etc.) through the delivery of electrical impulses that stimulate the muscle tissue beneath the user's skin. The electrode arrangement disclosed herein strategically positions individual pairs of electrodes on the user's body to prevent transthoracic flow of electrical current. As used herein, "transthoracic electrical current" or "transthoracic flow of electrical current" can mean electrical current that crosses either the midsagittal plane or the frontal plane of the user's body within the thoracic cavity.

In an illustrative example, the disclosed EMS suit may include a vest portion that is to be worn on an upper trunk of the user's body. The vest portion may comprise a left front portion, a right front portion, and a back portion. In some embodiments, the left front portion has a first pair of electrodes positioned on an inner surface of the left front portion and within a top half of the left front portion, while the right front portion has a second pair of electrodes positioned on an inner surface of the right front portion and within a top half of the right front portion. In this manner, when the body of a user is wearing the EMS suit, the first pair of electrodes may be disposed on (or atop) one or more left pectoral muscles of the body, and the first pair of electrodes may, therefore, be positioned on a first (e.g., left) side of a midsagittal plane of the body, as well as on a first (e.g., front) side of the frontal plane of the body. Meanwhile, the second pair of electrodes may be disposed on (or atop) one or more right pectoral muscles of the body, and the second pair of electrodes may, therefore, be positioned on a second (e.g., right) side of the midsagittal plane of the body, as well as on the first (e.g., front) side of the frontal plane of the body.

With the arrangement of electrodes described above, whenever electrical impulses are delivered by the respective pairs of electrodes, the flow of electrical current is isolated (or kept local) to each pair of electrodes. In other words, during operation of the EMS suit, electrical current does not flow between an electrode of the first pair of electrodes and an electrode of the second pair of electrodes, or any other pair for that matter. Said another way, electrical current does not flow from the first pair of electrodes to the second pair of electrodes, or vice versa. This means that electrical current does not flow across the midsagittal plane of the user's body in a region of the thoracic cavity during operation of the EMS suit. Instead, during a frame of a series of frames, a first pulse may be delivered via the first pair of electrodes, and a second pulse may be delivered via the second pair of electrodes subsequent to the first pulse, or vice versa. This is because the first pair of electrodes corresponds to a first channel, and the second pair of electrodes corresponds to a second channel, and electrical impulses are delivered via individual channels of multiple channels sequentially (or in sequence), one channel after another. Thus, at any given moment, a single pair of electrodes is "firing", and the electrical current takes the path of least resistance through the user's body (which acts as a resistor in the electrical circuit), and the flow of electrical current is thereby isolated to a region of the user's body where the single pair of actively firing electrodes are located. Accordingly, in a region of the thoracic cavity, electrical current flow is localized to individual muscle groups on one side of the midsagittal plane or the other, which is an ultra-conservative precautionary measure to prevent the flow of electrical current across the midsagittal plane in a region of the thoracic cavity. An EMS suit with such an arrangement of electrodes may eliminate a risk of transthoracic flow of electrical current. It follows that the EMS suit described herein is sufficiently safe to be sold without a prescription (e.g., over-the-counter), seeing as how the EMS suit can be used without risk of transthoracic electrical current.

In some embodiments, the back portion of the vest portion of the EMS suit has a third pair of electrodes positioned on an inner surface of the back portion and within a left half of the back portion, and a fourth pair of electrodes positioned on the inner surface of the back portion and within a right half of the back portion. In this manner, when the body of a user is wearing the EMS suit, the third pair of electrodes may be disposed on (or atop) one or more left back muscles of the body, and the third pair of electrodes may, therefore, be positioned on the first (e.g., left) side of a midsagittal plane of the body, as well as on a second (e.g., back) side of the frontal plane of the body. Meanwhile, the fourth pair of electrodes may be disposed on (or atop) one or more right back muscles of the body, and the fourth pair of electrodes may, therefore, be positioned on the second (e.g., right) side of the midsagittal plane of the body, as well as on the second (e.g., back) side of the frontal plane of the body.

With the described arrangement of electrodes in the back portion of the vest portion, whenever electrical impulses are delivered by the respective pairs of electrodes in the back portion, the flow of electrical current is isolated (or kept local) to each pair of electrodes. In other words, during operation of the EMS suit, electrical current does not flow between an electrode of the third pair of electrodes and an electrode of the fourth pair of electrodes, or any other pair for that matter. Said another way, electrical current does not flow from the third pair of electrodes to the fourth pair of electrodes, or vice versa. This, again, means that electrical current does not flow across the midsagittal plane of the user's body in a region of the thoracic cavity during operation of the EMS suit. Furthermore, with the disclosed electrode arrangements in the front and the back of the vest portion, electrical current also does not cross the frontal plane of the user's body in a region of the thoracic cavity during operation of the EMS suit. Instead, during a frame of a series of frames, a first pulse may be delivered via the first pair of electrodes, a second pulse may be delivered via the second pair of electrodes subsequent to the first pulse, a third pulse may be delivered via the third pair of electrodes subsequent to the second pulse, and a fourth pulse may be delivered via the fourth pair of electrodes subsequent to the third pulse, or in some other sequential ordering. This is because the first pair of electrodes corresponds to the first channel, the second pair of electrodes corresponds to the second channel, the third pair of electrodes corresponds to a third channel, and the fourth pair of electrodes corresponds to a fourth channel, and electrical impulses are delivered via individual channels of multiple channels sequentially (or in sequence), one channel after another. Thus, at any given moment, a single pair of electrodes is "firing", and the electrical current takes the path of least resistance through the user's body, and the flow of electrical current is thereby isolated to a region of the user's body where the single pair of actively firing electrodes are located. Accordingly, in a region of the thoracic cavity, electrical current flow is localized to individual muscle groups on one side of the midsagittal plane or the other, and on one side of the frontal plane or the other, which is an ultra-conservative precautionary measure to prevent the flow of electrical current across both the midsagittal plane and the frontal plane in a region of the thoracic cavity.

In some embodiments, in order to stimulate upper and middle back muscles, the back portion of the vest portion of the EMS suit may include at least four pairs of electrodes, each pair of electrodes being disposed on one side of the midsagittal plane of the body or the other when the body is wearing the EMS suit. For example, the back portion may have the aforementioned third and fourth pairs of electrodes, as well as a fifth pair of electrodes positioned on the inner surface of the back portion, within the left half of the back portion, and below the third pair of electrodes, as well as a sixth pair of electrodes positioned on the inner surface of the back portion, within the right half of the back portion, and below the fourth pair of electrodes. The third and fourth pairs of electrodes may be configured to stimulate the upper back muscles, while the fifth and sixth pairs of electrodes may be configured to stimulate the middle back muscles. Nevertheless, with this arrangement of electrodes in the back portion of the vest portion, the flow of electrical current does not cross the midsagittal plane or the frontal plane of the body in a region of the thoracic cavity during operation of the EMS suit for the reasons described herein.

In some embodiments, the EMS suit comprises at least two arm bands, including a left arm band and a right arm band. The left arm band may have a seventh pair of electrodes adjacent one another, and the right arm band may have an eighth pair of electrodes adjacent one another. In this manner, when the body of a user is wearing the EMS suit, the seventh pair of electrodes may be disposed on (or atop) one or more left arm muscles (e.g., left upper arm muscles) of the body, and the seventh pair of electrodes may, therefore, be positioned on the first (e.g., left) side of a midsagittal plane of the body. Meanwhile, the eighth pair of electrodes may be disposed on (or atop) one or more right arm muscles (e.g., right upper arm muscles) of the body, and the eighth pair of electrodes may, therefore, be positioned on the second (e.g., right) side of the midsagittal plane of the body.

With the described arrangement of electrodes in the arm bands, whenever electrical impulses are delivered by the respective pairs of electrodes in the respective arm bands, the flow of electrical current is isolated (or kept local) to each pair of electrodes (i.e., each arm band). In other words, during operation of the EMS suit, electrical current does not flow between an electrode of the seventh pair of electrodes and an electrode of the eighth pair of electrodes, or any other pair for that matter. Said another way, electrical current does not flow from the seventh pair of electrodes to the eighth pair of electrodes, or vice versa. This, again, means that electrical current does not flow across the midsagittal plane of the user's body in a region of the thoracic cavity during operation of the EMS suit. Rather, because the electrodes of a given pair correspond to a common channel, and because electrical impulses are delivered via individual channels of the multiple channels sequentially, a single pair of electrodes is actively firing at any given moment, thereby isolating the electrical current flow to the actively firing pair of electrodes, which means that electrical current does not cross the midsagittal plane (or the frontal plane) of the user's body in a region of the thoracic cavity during operation of the EMS suit.

The techniques and systems described herein may also allow for one or more devices to conserve resources with respect to communications bandwidth resources, processing resources, memory resources, power resources, and/or other resources, as described herein. Additional technical effects can also be realized from an implementation of the technologies disclosed herein. Described herein are example processes, as well as systems and devices comprising one or more processors and one or more memories, as well as non-transitory computer-readable media storing computer-executable instructions that, when executed, by one or more processors perform various acts and/or processes disclosed herein.

FIG. 1 is a schematic diagram of an illustrative EMS suit 100 having an arrangement of electrodes that prevents transthoracic electrical current, according to embodiments described herein. The EMS suit 100 may comprise a vest portion 102, a pants portion 104, and/or at least two arm bands 106 including a right arm band 106(1) and a left arm band 106(2). The vest portion 102 is to be worn on an upper trunk of a user's body. The pants portion 104 is to be worn on a lower trunk and/or legs (e.g., upper legs) of the user's body. The arm bands 106 are to be worn on arms (e.g., upper arms) of the user's body. To secure the EMS suit 100 on a user's body, each portion 102/104/106 of the EMS suit 100 may include one or more straps, fasteners (e.g., hook-and-loop fasteners, zippers, buttons, clips, latches, etc.) to secure and/or tighten various parts of the EMS suit 100 to ensure a snug, yet comfortable, fit of the EMS suit 100 on the user's body.

Figure 3A:
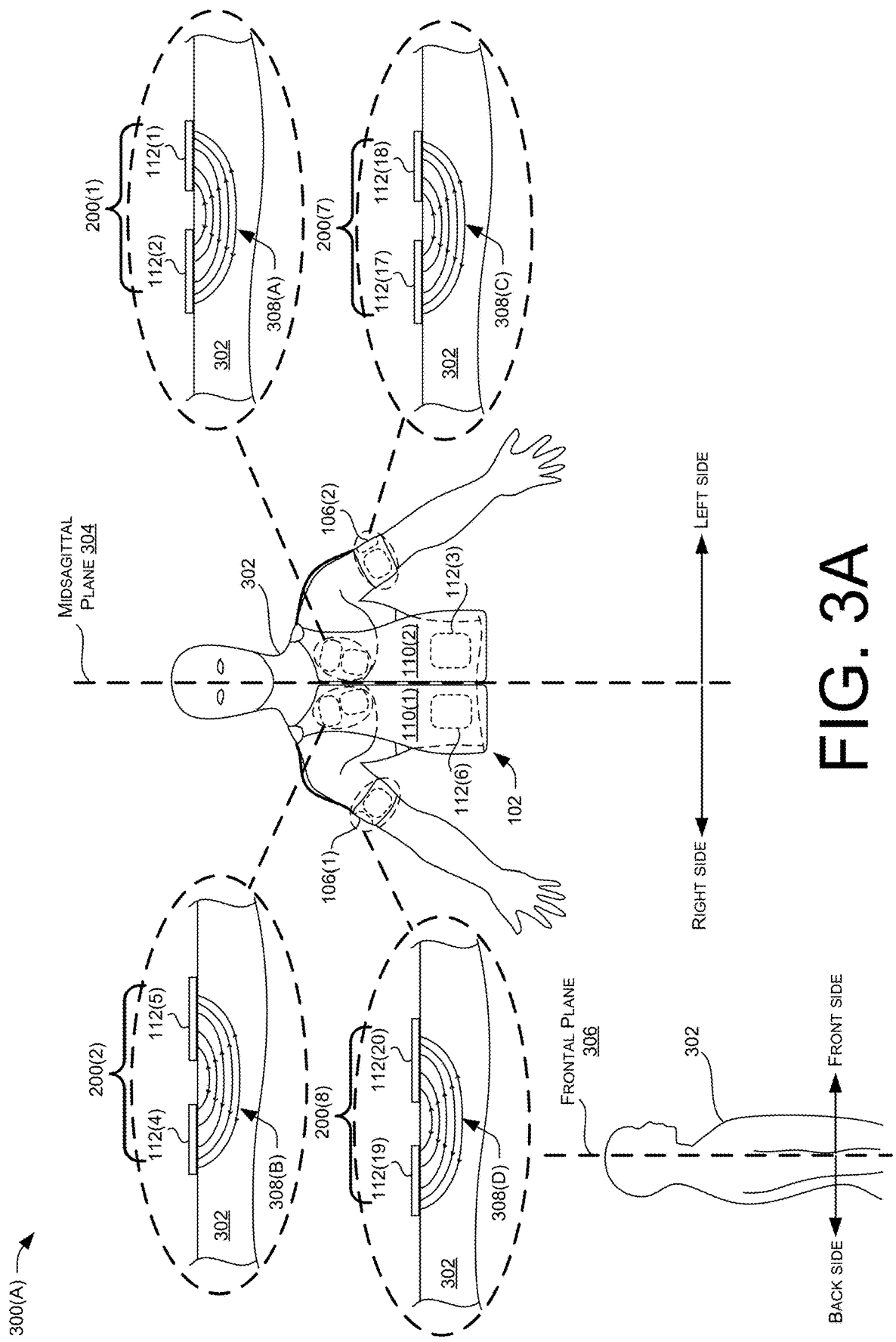
FIG. 3A is a schematic diagram illustrating how the arrangement of electrodes on the front of the vest portion and the arm bands of the disclosed EMS suit prevents transthoracic electrical current.
Figure 3B:
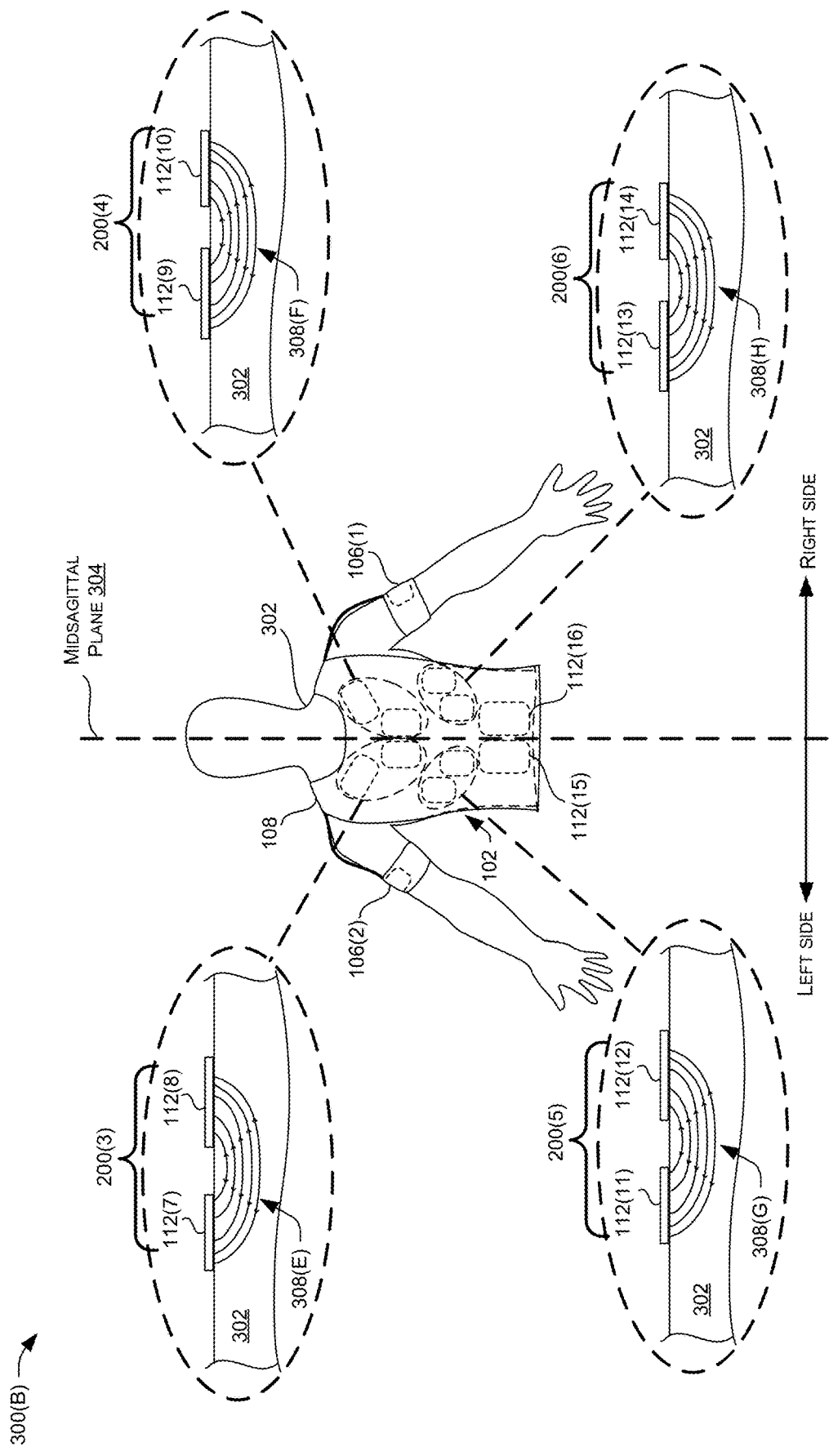
FIG. 3B is a schematic diagram illustrating how the arrangement of electrodes on the back of the vest portion of the disclosed EMS suit prevents transthoracic electrical current.

The vest portion 102 may comprise a back portion 108, a right front portion 110(1), and a left front portion 110(2). FIG. 1 depicts the vest portion 102, the pants portion 104, and the arm bands 106 as being laid out flat, such as when the EMS suit 100 is laid down flat on a table top. As such, FIG. 1 shows a front view of the inner surfaces of the respective portions 102/104/106 of the EMS suit 100. Accordingly, the back surfaces of the respective portions 102/104/106 are not visible in FIG. 1. When the vest portion 102 is worn by a user, the back portion 108 covers at least a portion of the user's back (e.g., the back of the upper trunk of the body), as shown in FIG. 3B, the right front portion 110(1) covers at least a portion of the user's right thorax and abdomen (e.g., the front-right half of the upper trunk of the body), as shown in FIG. 3A, and the left front portion 110(2) covers at least a portion of the user's left thorax and abdomen (e.g., the front-left half of the upper trunk of the body), as shown in FIG. 3A.

Each portion 102/104/106 of the EMS suit 100 may include one or more electrodes 112. FIG. 1 depicts multiple electrodes 112 on each portion 102/104/106 of the EMS suit 100, as an illustrative example. The electrodes 112 may be affixed to the EMS suit 100 in any suitable manner. For example, the electrodes 112 can be adhered or bonded to the suit 100 using an adhesive (e.g., glue), sewn into pockets or pouches of the EMS suit 100, etc. The dashed lines in FIG. 1 may represent stitching on the EMS suit 100, such as stitching that provides an enclosed pouch for each electrode 112 that is connected via internal wiring to electronics of, or connected to, the EMS suit 100 (e.g., electronics of an impulse pack). Accordingly, the electrodes 112 may be embedded in fabric of the EMS suit 100. This may mean that the electrodes 112 are permanently affixed to the EMS suit 100 (i.e., the user may be unable to remove, replace, and/or move the electrodes 112 without tearing apart the EMS suit 100 in a destructive manner). In some embodiments, the electrodes 112 may be removable (e.g., by housing the electrodes 112 within pockets or pouches that are openable (e.g., pouches with zippers or snap buttons to open and close the pouch for insertion/removal of the electrodes 112). In some embodiments, an individual electrode 112 and at least some wiring connected thereto may be secured within a pouch using a rivet or a similar fastener during fabrication of the EMS suit.

In FIG. 1, the left front portion 110(2) of the vest portion 102 has a first pair of electrodes, 112(1) and 112(2), corresponding to a common channel of multiple channels. These electrodes 112(1) and 112(2) may be positioned on an inner surface of the vest portion 102, positioned adjacent one another, and/or positioned within a top half of the left front portion 110(2). Accordingly, the first pair of electrodes, 112(1) and 112(2), may be disposed on one or more left pectoral muscles, and may be positioned on a first (e.g., left) side of a midsagittal plane, of the user's body when the user's body is wearing the EMS suit 100. In different configurations of the vest portion 102, the first pair of electrodes, 112(1) and 112(2), may not be positioned in the top half of the left front portion 110(2) and/or adjacent one another, yet, when the vest portion 102 is worn by a user, the first pair of electrodes, 112(1) and 112(2), are still disposed on one or more left pectoral muscles. As used herein, "adjacent" can mean within a threshold distance, as measured from an edge of one electrode 112 to the edge of another electrode 112. The electrodes 112 may be of any suitable size (e.g., 2 inches×2 inches, 4 inches×4 inches, etc.) and any suitable shape (e.g., a rectangular shape, circular shape, triangular shape, etc.). Depending on type of muscles that a pair of electrodes 112 are configured to stimulate, the pair of electrodes may be spaced closer to each other or farther apart from each other. As an example, for larger muscles, it may be desirable to space electrodes 112 farther apart, as compared to a smaller spacing of electrodes 112 used for smaller muscles. In addition, the EMS suit 100 may come in different sizes for different users of varying body types (e.g., big users, small users, etc.). Accordingly, the size of the EMS suit 100 may dictate the exact spacing of a pair of electrodes 112. In fact, a given pair of electrodes 112 that correspond to a common channel may, in some embodiments, be spaced relatively far from one another on the EMS suit 100 such that the pair of electrodes 112 may not be considered to be adjacent one another. For example, one electrode 112 of a pair of electrodes may be positioned on the pants portion 104 and the other electrode 112 of the pair may be positioned on the vest portion 102, and pairs are not limited herein to being disposed on a common portion 102/104/106 of the EMS suit 100. In any case, a threshold distance used to define whether electrodes 112 are adjacent one another or not adjacent one another may be a threshold distance no greater than about 4 inches, no greater than about 3 inches, no greater than about 2 inches, no greater than about 1 inch, or no greater than about 0.5 inches.

Furthermore, at least some of the electrodes 112 may be oriented at an angle relative to vertical or horizontal, as shown in FIG. 1. For example, in the vest portion 102, the electrodes 112(1), 112(2), 112(4), 112(5), 112(7), and 112(9) are angled relative to vertical or horizontal, which may be done to optimize coverage area of the electrodes 112 on particular muscle groups (e.g., pectorals, rhomboids, etc.). Similarly, the electrodes 112 in the pants portion 104 are shown as being angled relative to vertical or horizontal with the upright orientation of the pants portion 104 shown in FIG. 1.

The left front portion 110(2) may further include a first additional electrode 112(3) positioned on the inner surface of the vest portion 102 and within a bottom half of the left front portion 110(2). Accordingly, the first additional electrode 112(3) may be disposed on one or more left abdominal muscles, and may be positioned on the first (e.g., left) side of the midsagittal plane, of the user's body when the user's body is wearing the EMS suit 100.

In FIG. 1, the right front portion 110(1) of the vest portion 102 has a second pair of electrodes, 112(4) and 112(5), corresponding to a common channel of multiple channels. These electrodes 112(4) and 112(5) may be positioned on the inner surface of the vest portion 102, positioned adjacent one another, and/or positioned within a top half of the right front portion 110(1). Accordingly, the second pair of electrodes, 112(4) and 112(5), may be disposed on one or more right pectoral muscles, and may be positioned on a second (e.g., right) side of the midsagittal plane, of the user's body when the user's body is wearing the EMS suit 100. In different configurations of the vest portion 102, the second pair of electrodes, 112(4) and 112(5), may not be positioned in the top half of the right front portion 110(1) and/or adjacent one another, yet, when the vest portion 102 is worn by a user, the second pair of electrodes, 112(4) and 112(5), are still disposed on one or more right pectoral muscles. The right front portion 110(1) may further include a second additional electrode 112(6) positioned on the inner surface of the vest portion 102 and within a bottom half of the right front portion 110(1). Accordingly, the second additional electrode 112(6) may be disposed on one or more right abdominal muscles, and may be positioned on the second (e.g., right) side of the midsagittal plane, of the user's body when the user's body is wearing the EMS suit 100. The first additional electrode 112(3) on the left front portion 110(2) and the second additional electrode 112(6) on the right front portion 110(1) may form a pair of electrodes that correspond to a common channel of multiple channels, as defined herein. That is, electrical current may flow between the first additional electrode 112(3) and the second additional electrode 112(6) during operation of the EMS suit 100, which may cross the midsagittal plane of the user's body, but this electrical current is restricted to a region of the abdominal cavity and is not within a region of the thoracic cavity.

The back portion 108 of the vest portion 102 may include a third pair of electrodes, 112(7) and 112(8), corresponding to a common channel of multiple channels. These electrodes 112(7) and 112(8) may be positioned on the inner surface of the vest portion 102, positioned adjacent one another, and/or positioned within a left half of the back portion 108. The back portion 108 of the vest portion 102 may further include a fourth pair of electrodes, 112(9) and 112(10), corresponding to a common channel of multiple channels. These electrodes 112(9) and 112(10) may be positioned on the inner surface of the vest portion 102, positioned adjacent one another, and/or positioned within a right half of the back portion 108. In some embodiments, the back portion 108 may further include a fifth pair of electrodes, 112(11) and 112(12), corresponding to a common channel of multiple channels. These electrodes 112(11) and 112(12) may be positioned on the inner surface of the vest portion 102, positioned adjacent one another, positioned within the left half of the back portion 108, and/or positioned below the third pair of electrodes, 112(7) and 112(8). In some embodiments, the back portion 108 may further include a sixth pair of electrodes, 112(13) and 112(14), corresponding to a common channel of multiple channels. These electrodes 112(13) and 112(14) may be positioned on the inner surface of the vest portion 102, positioned adjacent one another, positioned within the right half of the back portion 108, and/or positioned below the fourth pair of electrodes, 112(9) and 112(10). The back portion 108 may further include a third additional electrode 112(15) positioned on the inner surface of the vest portion 102 and within a bottom half and left half of the back portion 108, as well as a fourth additional electrode 112(16) positioned on the inner surface of the vest portion 102 and within the bottom half and right half of the back portion 108. The third additional electrode 112(15) and the fourth additional electrode 112(16) may form a pair of electrodes that correspond to a common channel of multiple channels, as defined herein. That is, electrical current may flow between the third additional electrode 112(15) and the fourth additional electrode 112 (16) during operation of the EMS suit 100, which may cross the midsagittal plane of the user's body, but this electrical current is restricted to a region of the abdominal cavity and is not within a region of the thoracic cavity.

With the described electrode arrangement in the back portion 108, the third pair of electrodes, 112(7) and 112(8), may be disposed on one or more left upper back muscles, and may be positioned on the first (e.g., left) side of the midsagittal plane, of the user's body when the user's body is wearing the EMS suit 100, as shown in FIG. 3B. The fourth pair of electrodes, 112(9) and 112(10), may be disposed on one or more right upper back muscles, and may be positioned on the second (e.g., right) side of the midsagittal plane, of the user's body when the user's body is wearing the EMS suit 100, as shown in FIG. 3B. The fifth pair of electrodes, 112(11) and 112(12), may be disposed on one or more left middle back muscles, and may be positioned on the first (e.g., left) side of the midsagittal plane, of the user's body when the user's body is wearing the EMS suit 100, as shown in FIG. 3B. The sixth pair of electrodes, 112(13) and 112(14), may be disposed on one or more right middle back muscles, and may be positioned on the second (e.g., right) side of the midsagittal plane, of the user's body when the user's body is wearing the EMS suit 100, as shown in FIG. 3B. In addition, the third additional electrode 112 (15) may be disposed on one or more left lower back muscles, and may be positioned on the first (e.g., left) side of the midsagittal plane, of the user's body when the user's body is wearing the EMS suit 100, as shown in FIG. 3B. Finally, the fourth additional electrode 112(16) may be disposed on one or more right lower back muscles, and may be positioned on the second (e.g., right) side of the midsagittal plane, of the user's body when the user's body is wearing the EMS suit 100, as shown in FIG. 3B.

FIG. 1 also shows that the vest portion 102 may include one or more straps 114 that connect the back portion 108 to one or both of the left front portion 110(2) and the right front portion 110(1). These straps 114 may be removably coupled to the back portion 108 and/or the respective front portion 110 to allow for completely decoupling the back portion 108 from one or both of the left front portion 110(2) and/or the right front portion 110(1). Alternatively, the straps 114 may be permanently affixed to one or more of the respective portions 108/110 of the vest portion 102. The straps 114 may be flexible and stretchable to provide a comfortable fit when the EMS suit 100 is worn, and to accommodate users of different body types. In some embodiments, the straps 114 may be omitted and the vest portion 102 may be a single piece of fabric that can still be partitioned into the portions 108, 110(1), and 110(2) for referencing the placement, or the positioning, of the electrodes 112 in/on the EMS suit 100. In some embodiments, the vest portion 102 may be a single piece of fabric and may still include straps similar to the straps 114, which may be internal to the fabric of the vest (i.e., not visible to the user), and/or which may be disposed on the outer surface of the vest portion 102 and usable to tighten or loosen the fit of the vest portion 102.

One or more straps 116 may also connect the back portion 108 to the pants portion 104. The strap(s) 116 may also be removably coupled to the back portion 108 and/or the pants portion 104 to allow for completely decoupling the back portion 108 from the pants portion 104. Alternatively, the strap(s) 116 may be permanently affixed to one or more of the respective portions 108/104. The strap(s) 116 may also be flexible and stretchable to provide a comfortable fit when the EMS suit 100 is worn, and to accommodate users of different body types. In some embodiments, the straps(s) 116 may be omitted.

The vest portion 102 may further include at least two arm band connectors 118 including a right arm band connector 118(1) and a left arm band connector 118(2). The right arm band connector 118(1) is configured to couple to the right arm band 106(1) and to provide an electrical connection (e.g., a wired connection) from electronics in the vest portion 102 that deliver electrical impulses. Similarly, the left arm band connector 118(2) is configured to couple to the left arm band 106(2) and to provide an electrical connection (e.g., a wired connection) from electronics in the vest portion 102 that deliver electrical impulses via the electrodes 112 of the left arm band 106(2). It is to be appreciated, however, that one or more of the electrodes 112 of the EMS suit 100 may be wirelessly connected to electronics (e.g., to a processor(s)) using a wireless protocol (e.g., Bluetooth®, ZIGBEE, WiFi, etc.).

The left arm band 106(2) is shown as having a seventh pair of electrodes, 112(17) and 112(18), corresponding to a common channel of multiple channels. These electrodes 112(17) and 112(18) may be positioned on an inner surface of the left arm band 106(2) and/or positioned adjacent one another. The right arm band 106(1) is shown as having an eighth pair of electrodes, 112(19) and 112(20), corresponding to a common channel of multiple channels. These electrodes 112(19) and 112(20) may be positioned on an inner surface of the right arm band 106(1) and/or positioned adjacent one another. The seventh pair of electrodes, 112(17) and 112(18), may be disposed on one or more left (e.g., upper) arm muscles, and may be positioned on the first (e.g., left) side of the midsagittal plane, of the user's body when the body is wearing the EMS suit 100, as shown in FIG. 3A. The eighth pair of electrodes 112(19) and 112(20) may be disposed on one or more right (e.g., upper) arm muscles, and may be positioned on the second (e.g., right) side of the midsagittal plane, of the user's body when the body is wearing the EMS suit 100, as shown in FIG. 3A.

The pants portion 104 may have an electrode 112(21) positioned on an inner surface of the pants portion 104 and/or positioned within a top half and right half of the pants portion 104 for delivery of electrical impulses to right glute muscles. The pants portion 104 may further have an electrode 112(22) positioned on an inner surface of the pants portion 104 and/or positioned within the top half and left half of the pants portion 104 for delivery of electrical impulses to left glute muscles. The pants portion 104 may further have an electrode 112(23) positioned on the inner surface of the pants portion 104 and/or positioned near a bottom and in the right half of the pants portion 104 for delivery of electrical impulses to right hamstring muscles. The pants portion 104 may further have an electrode 112(24) positioned on the inner surface of the pants portion 104 and/or positioned near the bottom and in the left half of the pants portion 104 for delivery of electrical impulses to left hamstring muscles. The pants portion 104 may further have an electrode 112(25) positioned on the inner surface of the pants portion 104 and/or positioned near the bottom and in the right half of the pants portion 104 for delivery of electrical impulses to right quadricep muscles. The pants portion 104 may further have an electrode 112(26) positioned on the inner surface of the pants portion 104 and/or positioned near the bottom and in the left half of the pants portion 104 for delivery of electrical impulses to left quadricep muscles. The electrode 112(21) and the electrode 112(22) positioned on the top half of the pants portion 104 may form a pair of electrodes that correspond to a common channel of multiple channels, as defined herein. That is, electrical current may flow between the electrode 112(21) and the electrode 112(22) during operation of the EMS suit 100, which may cross the midsagittal plane of the user's body, but this electrical current is restricted to a region of the user's glute muscles and is not within a region of the thoracic cavity. The electrode 112(23) and the electrode 112(24) positioned near the bottom of the pants portion 104 may form a pair of electrodes that correspond to a common channel of multiple channels, as defined herein. That is, electrical current may flow between the electrode 112(23) and the electrode 112(24) during operation of the EMS suit 100, but not in a region of the thoracic cavity. The electrode 112(25) and the electrode 112(26) positioned near the bottom of the pants portion 104 may form a pair of electrodes that correspond to a common channel of multiple channels, as defined herein. That is, electrical current may flow between the electrode 112(25) and the electrode 112(26) during operation of the EMS suit 100, but not in a region of the thoracic cavity. Alternatively, the electrode 112(23) and the electrode 112(25) may form a pair of electrodes that correspond to a common channel of multiple channels, and the electrode 112(24) and the electrode 112(26) may form a pair of electrodes that correspond to a common channel of multiple channels. That is, electrical current may flow between the electrode 112(23) and the electrode 112(25), and between the electrode 112(24) and the electrode 112(26), but not in a region of the thoracic cavity.

With the placement, or positioning, of electrodes 112 in/on the EMS suit 100 shown in FIG. 1, flow of electrical current in a region of the thoracic cavity can be isolated on one side or the other of the midsagittal plane and on one side or the other of the frontal plane of the user's body during operation of the EMS suit 100. This is illustrated in FIGS. 3A and 3B.

Figure 2A:
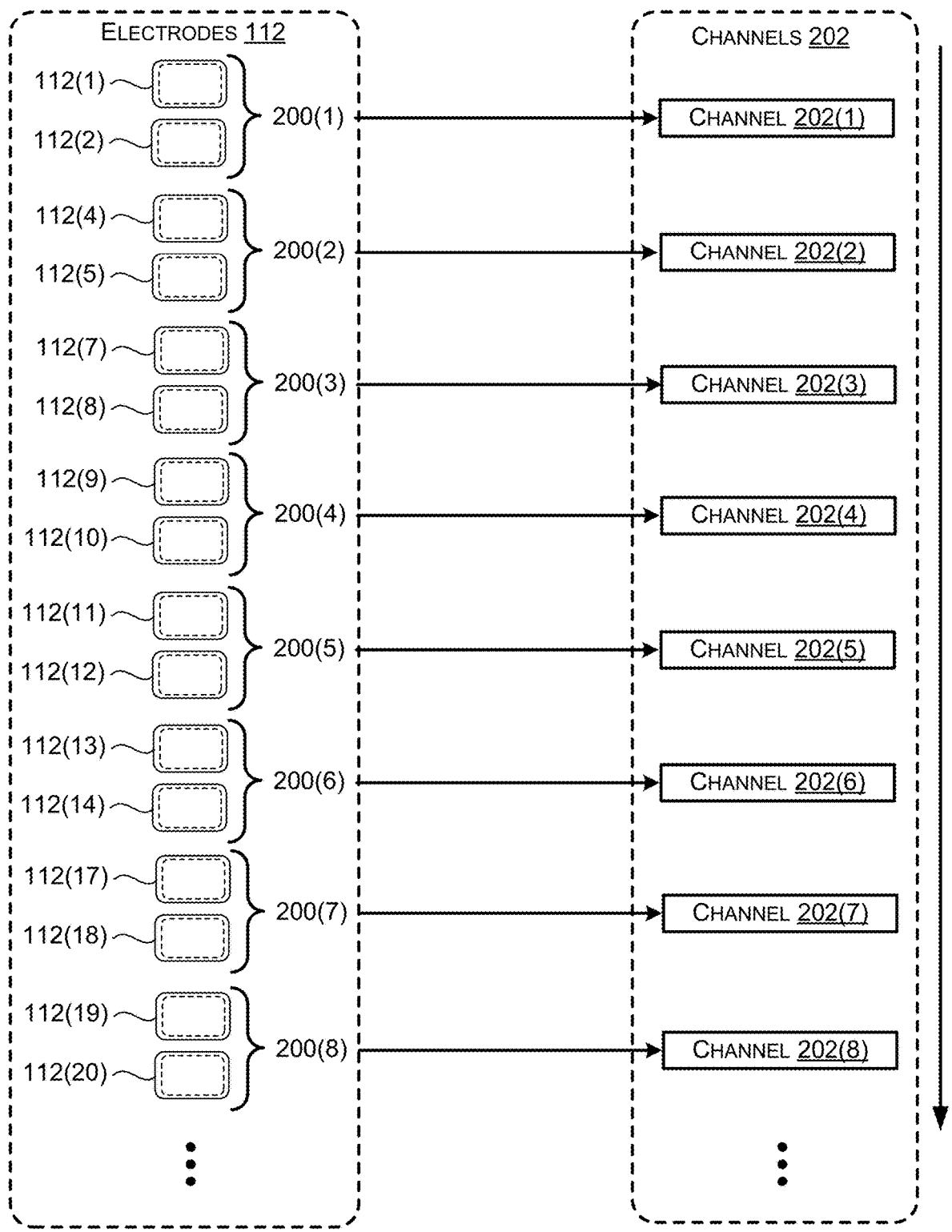
FIGS. 2A and 2B illustrate a schematic diagram illustrating how pairs of electrodes correspond to channels for delivery of electrical impulses one channel after another.
Figure 2B:
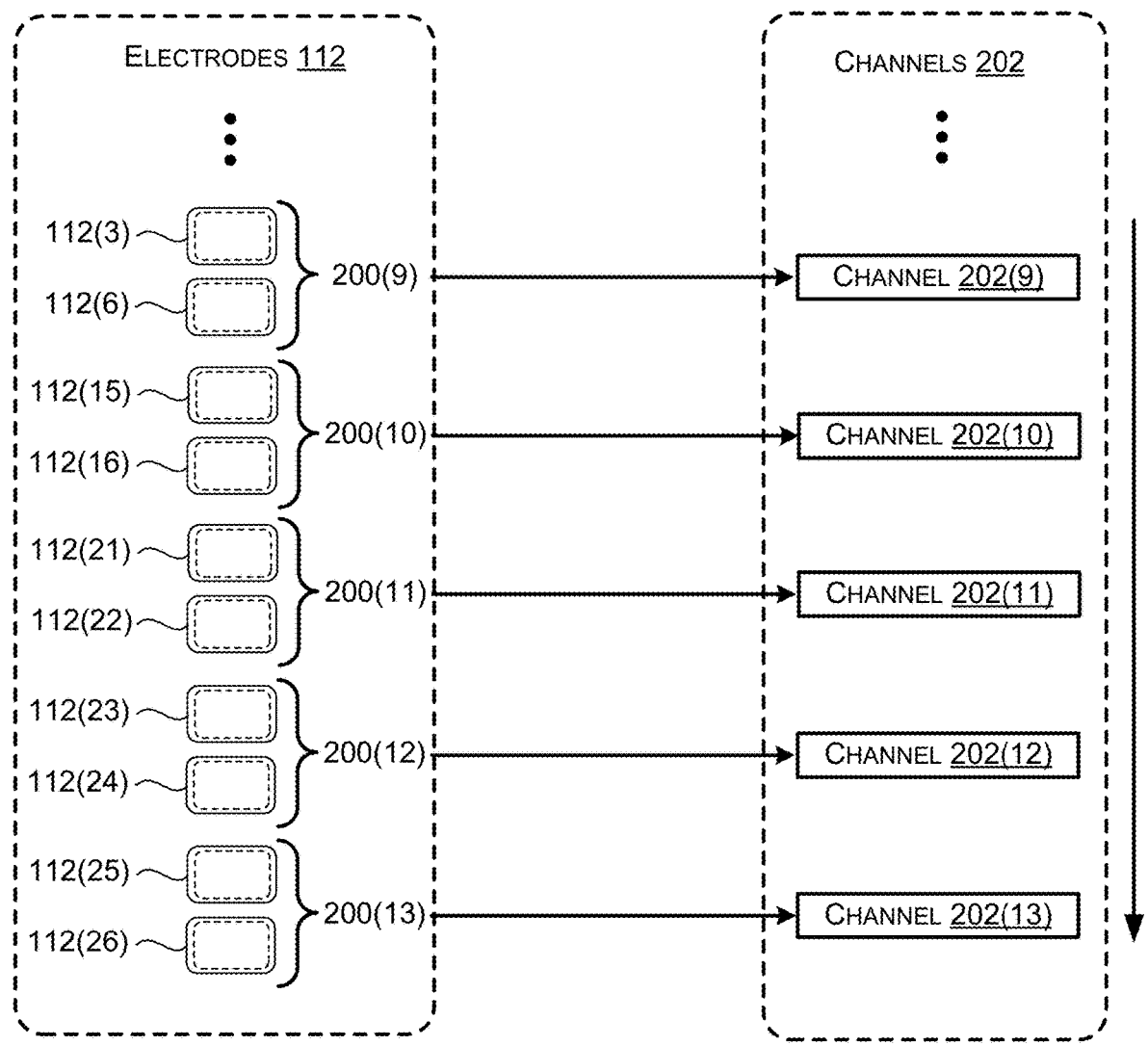

FIGS. 2A and 2B illustrate a schematic diagram illustrating how pairs 200 of electrodes 112 correspond to channels 202 for delivery of electrical impulses one channel 202 after another. One or more processors of the EMS suit 100, and/or of a system including the EMS suit 100, may cause circuitry of the EMS suit 100 to deliver electrical impulses to individual channels 202 of multiple channels 202(1)-(13) sequentially (or in the sequence), one channel 202 after another, and in accordance with pulse parameter settings (e.g., intensity (amplitude), pulse width, etc.). Although FIGS. 2A and 2B show an example where the number of channels is equal to 13 channels, it is to be appreciated that any number of "N" channels 202 can be used, where "N" is any positive integer, such as an integer less than 13, or greater than 13. During operation of the EMS suit 100, frames are processed at a frame rate. For a frame rate of 90 Hertz (Hz), this would mean that output is serially provided across the N channels (e.g., where N=13) at a rate of 90 times per second. In other words, electrical impulses would be delivered to channels 202(1)-(13) sequentially (or in the sequence) during a frame, and this would occur 90 times a second (e.g., 90 frames processed in one second). For example, during a frame, a first electrical impulse (or pulse) may be delivered via the first pair of electrodes 200(1) corresponding to a first channel 202(1), followed by a second electrical impulse (or pulse) delivered via the second pair of electrodes 200(2) corresponding to a second channel 202(2), and so on and so forth for any suitable number of N channels. In the example of FIGS. 2A and 2B, a first pair of electrodes 200(1) includes the electrodes 112(1) and 112(2) introduced in FIG. 1, a second pair of electrodes 200(2) includes the electrodes 112(4) and 112(5) introduced in FIG. 1, a third pair of electrodes 200(3) includes the electrodes 112(7) and 112(8) introduced in FIG. 1, a fourth pair of electrodes 200(4) includes the electrodes 112(9) and 112(10) introduced in FIG. 1, a fifth pair of electrodes 200(5) includes the electrodes 112(11) and 112(12) introduced in FIG. 1, a sixth pair of electrodes 200(6) includes the electrodes 112(13) and 112(14) introduced in FIG. 1, a seventh pair of electrodes 200(7) includes the electrodes 112(17) and 112(18) introduced in FIG. 1, an eighth pair of electrodes 200(8) includes the electrodes 112(19) and 112(20) introduced in FIG. 1, a ninth pair of electrodes 200(9) includes the electrodes 112(3) and 112(6) introduced in FIG. 1, a tenth pair of electrodes 200(10) includes the electrodes 112(15) and 112(16) introduced in FIG. 1, an eleventh pair of electrodes 200(11) includes the electrodes 112(21) and 112(22) introduced in FIG. 1, a twelfth pair of electrodes 200(12) includes the electrodes 112(23) and 112(24) introduced in FIG. 1, and a thirteenth pair of electrodes 200(13) includes electrodes 112(25) and 112(26). Because the number of channels 202 may be less than 13 channels, or greater than 13 channels, in some embodiments, it is to be appreciated that any number of "P" electrodes 112 can be used, where "P" is any positive integer greater than N, where N represents the number of channels 202 (e.g., P may equal N×2, for twice the number of electrodes 112 as there are channels 202). Although FIGS. 2A and 2B depict a particular ordering of electrode pairs 200 (pairs 200(1)-(13)) and channels 202 (e.g., channels 202(1)-(13)), it is to be appreciated that the ordering of electrode pairs 200 and channels 202 shown in FIGS. 2A and 2B is nonlimiting in the present disclosure, and, therefore, it is to be appreciated that electrode pairs 200 can be fired in any suitable sequence, such as by ordering them differently relative to the ordering shown in FIGS. 2A and 2B. Furthermore, as described herein, due to the arrangement of the electrodes 112 in a region of the thoracic cavity of the user, transthoracic flow of electrical current is prevented.

FIG. 3A is a schematic diagram 300(A) illustrating how the arrangement of electrodes 112 on the front portions 110 of the vest portion 102 and the arm bands 106 of the disclosed EMS suit 100 prevents transthoracic electrical current. FIG. 3A shows how the first pair of electrodes 200(1) may be disposed on one or more left pectoral muscles of the user's body 302, and may be positioned on a first (e.g., left) side of a midsagittal plane 304 of the user's body 302, when the user's body 302 is wearing the EMS suit 100. A frontal plane 306 of the user's body 302 is also shown in FIG. 3A. Accordingly, it can be appreciated that the first pair of electrodes 200(1) may be positioned on a first (e.g., front) side of the frontal plane 306 of the user's body 302 when the user's body 302 is wearing the EMS suit 100. Similarly, FIG. 3A shows how the second pair of electrodes 200(2) may be disposed on one or more right pectoral muscles of the user's body 302, and may be positioned on a second (e.g., right) side of the midsagittal plane 304 of the user's body 302, when the user's body 302 is wearing the EMS suit 100. It can be appreciated that the second pair of electrodes 200(2) may be positioned on the first (e.g., front) side of the frontal plane 306 of the user's body 302 when the user's body 302 is wearing the EMS suit 100.

During operation of the EMS suit 100, electrical current does not flow between either electrode, 112(1) or 112(2), of the first pair of electrodes 200(1) and either electrode, 112(4) or 112(5), of the second pair of electrodes 200(2), or any other pair 200 for that matter, based on first electrical impulses delivered via the first pair of electrodes 200(1) or based on second electrical impulses delivered via the second pair of electrodes 200(2). In other words, electrical current does not cross the midsagittal plane 304 of the user's body 302 in a region of the thoracic cavity during operation of the EMS suit 100. Rather, as depicted in FIG. 3A, because the electrodes 112(1) and 112(2) (of the first pair 200(1)) correspond to a common channel 202(1), the electrical current 308(A) travels from one electrode to the other of the first pair of electrodes 200(1), through the user's body 302, thereby isolating the electrical current 308(A) flow to the first pair of electrodes 200(1), and the muscle tissue beneath and/or near the first pair of electrodes 200(1). Similarly, as depicted in FIG. 3A, because the electrodes 112(4) and 112(5) (of the second pair 200(2)) correspond to a common channel 202(2), the electrical current 308(B) travels from one electrode to the other of the second pair of electrodes 200(2), through the user's body 302, thereby isolating the electrical current 308(B) flow to the second pair of electrodes 200(2), and the muscle tissue beneath and/or near the second pair of electrodes 200(2). Furthermore, in the left arm band 106(2), because the electrodes 112(17) and 112(18) (of the seventh pair 200(7)) correspond to a common channel 202(7), the electrical current 208(C) travels from one electrode to the other of the seventh pair of electrodes 200(7), through the user's body 302, thereby isolating the electrical current 308(C) flow to the seventh pair of electrodes 200(7), and the muscle tissue beneath and/or the seventh pair of electrodes 200(7). Likewise, in the right arm band 106(1), because the electrodes 112(19) and 112(20) (of the eighth pair 200(8)) correspond to a common channel 202(8), the electrical current 308(D) travels from one electrode to the other of the eighth pair of electrodes 200(8), through the user's body 302, thereby isolating the electrical current 308(D) flow to the eighth pair of electrodes 200(8), and the muscle tissue beneath and/or near the eighth pair of electrodes 200(8). Thus, in a region of the thoracic cavity, electrical current 308 flow is localized to individual muscle groups on one side of the midsagittal plane 304 or the other to prevent the flow of electrical current across the midsagittal plane 304 in a region of the thoracic cavity. An EMS suit 100 with such an arrangement of electrodes 112 may eliminate a risk of transthoracic flow of electrical current.

FIG. 3B is a schematic diagram 300(B) illustrating how the arrangement of electrodes 112 on the back portion 108 of the vest portion 102 of the disclosed EMS suit 100 prevents transthoracic electrical current. FIG. 3B shows how the third pair of electrodes 200(3) may be disposed on one or more left upper back muscles of the user's body 302, and may be positioned on the first (e.g., left) side of the midsagittal plane 304 of the user's body 302, when the user's body 302 is wearing the EMS suit 100. It can also be appreciated that the third pair of electrodes 200(3) may be positioned on a second (e.g., back) side of the frontal plane 306 of the user's body 302 when the user's body 302 is wearing the EMS suit 100. FIG. 3B further shows how the fourth pair of electrodes 200(4) may be disposed on one or more right upper back muscles of the user's body 302, and may be positioned on the second (e.g., right) side of the midsagittal plane 304 of the user's body 302, when the user's body 302 is wearing the EMS suit 100. It can also be appreciated that the fourth pair of electrodes 200(4) may be positioned on the second (e.g., back) side of the frontal plane 306 of the user's body 302 when the user's body 302 is wearing the EMS suit 100. FIG. 3B further shows how the fifth pair of electrodes 200(5) may be disposed on one or more left middle back muscles of the user's body 302 (and therefore positioned below the third pair of electrodes 200 (3)), and may be positioned on the first (e.g., left) side of the midsagittal plane 304 of the user's body 302, when the user's body 302 is wearing the EMS suit 100. It can also be appreciated that the fifth pair of electrodes 200(5) may be positioned on the second (e.g., back) side of the frontal plane 306 of the user's body 302 when the user's body 302 is wearing the EMS suit 100. FIG. 3B further shows how the sixth pair of electrodes 200(6) may be disposed on one or more right middle back muscles of the user's body 302 (and therefore positioned below the fourth pair of electrodes 200(4)), and may be positioned on the second (e.g., right) side of the midsagittal plane 304 of the user's body 302, when the user's body 302 is wearing the EMS suit 100. It can also be appreciated that the sixth pair of electrodes 200(6) may be positioned on the second (e.g., back) side of the frontal plane 306 of the user's body 302 when the user's body 302 is wearing the EMS suit 100.

During operation of the EMS suit 100, electrical current does not flow between either electrode, 112(7) or 112(8), of the third pair of electrodes 200(3) and either electrode, 112(9) or 112(10), of the fourth pair of electrodes 200(4), or any other pair 200 for that matter, based on third electrical impulses delivered via the third pair of electrodes 200(3) or based on fourth electrical impulses delivered via the fourth pair of electrodes 200(4). Similarly, electrical current does not flow between either electrode, 112(11) or 112(12), of the fifth pair of electrodes 200(5) and either electrode, 112(13) or 112(14), of the sixth pair of electrodes 200(6), or any other pair 200 for that matter, based on fifth electrical impulses delivered via the fifth pair of electrodes 200(5) or based on sixth electrical impulses delivered via the sixth pair of electrodes 200(6). In other words, electrical current does not cross the midsagittal plane 304 of the user's body 302 in a region of the thoracic cavity during operation of the EMS suit 100. Rather, as depicted in FIG. 3B, because the electrodes 112(7) and 112(8) (of the third pair 200(3)) correspond to a common channel 202(3), the electrical current 308(E) travels from one electrode to the other of the third pair of electrodes 200(3), through the user's body 302, thereby isolating the electrical current 308(E) flow to the third pair of electrodes 200(3), and the muscle tissue beneath and/or near the third pair of electrodes 200(3). Similarly, as depicted in FIG. 3B, because the electrodes 112(9) and 112(10) (of the fourth pair 200(4)) correspond to a common channel 202(4), the electrical current 308(F) travels from one electrode to the other of the fourth pair of electrodes 200(4), through the user's body 302, thereby isolating the electrical current 308(F) flow to the fourth pair of electrodes 200(4), and the muscle tissue beneath and/or near the fourth pair of electrodes 200(4). Furthermore, because the electrodes 112(11) and 112(12) (of the fifth pair 200(5)) correspond to a common channel 202(5), the electrical current 308(G) travels from one electrode to the other of the fifth pair of electrodes 200(5), through the user's body 302, thereby isolating the electrical current 308(G) flow to the fifth pair of electrodes 200(5), and the muscle tissue beneath and/or near the fifth pair of electrodes 200(5). Likewise, because the electrodes 112(13) and 112(14) (of the sixth pair 200(6)) correspond to a common channel 202(6), the electrical current 308(H) travels from one electrode to the other of the sixth pair of electrodes 200(6), through the user's body 302, thereby isolating the electrical current 308(H) flow to the sixth pair of electrodes 200(6), and the muscle tissue beneath and/or near the sixth pair of electrodes 200(6). Thus, in a region of the thoracic cavity, electrical current 308 flow is localized to individual muscle groups on one side of the midsagittal plane 304 or the other to prevent the flow of electrical current across the midsagittal plane 304 in a region of the thoracic cavity. An EMS suit 100 with such an arrangement of electrodes 112 may eliminate a risk of transthoracic flow of electrical current.

Furthermore, electrical current 308 does not cross the frontal plane 306 of the user's body 302 in a region of the thoracic cavity during operation of the EMS suit 100. Instead, the flow of electrical current is also kept local to the front of the body 302 or the back of the body 302 in a region of the thoracic cavity such that a risk of transthoracic flow of electrical current is eliminated.

Figure 4:
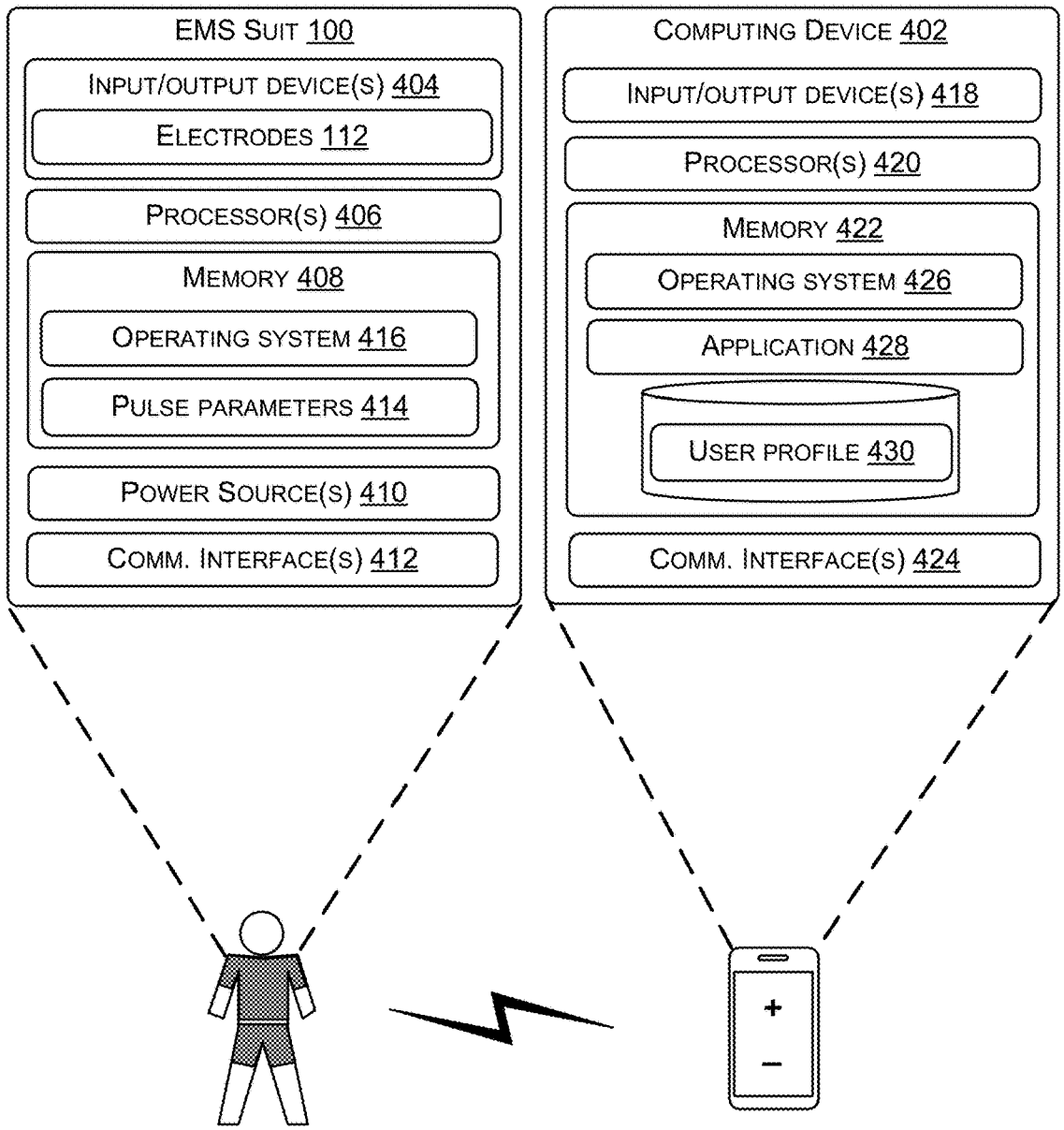
FIG. 4 illustrates block diagrams of a system that may include an EMS suit and a personal computing device, according to embodiments described herein.

FIG. 4 illustrates block diagrams of a system 400 that may include an EMS suit 100 and a personal computing device 402, among other components/devices, according to embodiments described herein. The EMS suit 100 is shown as including one or more input/output (I/O) devices 404. For example, the I/O devices 404 may include one or more microphones to receive audio input, such as user voice input. In some implementations, one or more cameras or other types of sensors may function as input devices to receive gestural input. In some embodiments, additional input devices may be provided in the form of a keyboard, keypad, touch screen, control buttons and the like.

The output devices, meanwhile, may include the electrodes 112, as described herein, as well as display(s), light element (e.g., LED), a vibrator to create haptic sensations, a speaker(s) (e.g., headphones), and/or the like. With reference to the electrodes 112, electrical impulses (or pulses) may be delivered via the electrodes 112, which may be controlled via instructions received from a processor(s) of the system 400 (e.g., to control initiation, cessation, duration, channels 202, and/or intensity of the electrical impulses).

The EMS suit 100 is shown as including one or more processors 406, memory 408 (or non-transitory computer-readable media 408), power source(s) 410, and a communications interface(s) 412. In some implementations, the processors(s) 406 may include a central processing unit(s) (CPU(s)), a graphics processing unit(s) (GPU(s)), both CPU(s) and GPU(s), a microprocessor(s), a digital signal processor(s) or other processing units or components known in the art. Alternatively, or in addition, the functionally described herein can be performed, at least in part, by one or more hardware logic components. For example, and without limitation, illustrative types of hardware logic components that can be used include field-programmable gate arrays (FPGAs), application-specific integrated circuits (ASICs), application-specific standard products (ASSPs), system-on-a-chip systems (SOCs), complex programmable logic devices (CPLDs), etc. Additionally, each of the processor(s) 406 may possess its own local memory, which also may store program modules, program data, and/or one or more operating systems.

The memory 408 may include volatile and nonvolatile memory, removable and non-removable media implemented in any method or technology for storage of information, such as computer-readable instructions, data structures, program modules, or other data. The memory 408 may be implemented as computer-readable storage media ("CRSM"), which may be any available physical media accessible by the processor(s) 406 to execute instructions stored on the memory 408. In one basic implementation, CRSM may include random access memory ("RAM") and Flash memory. In other implementations, CRSM may include, but is not limited to, read-only memory ("ROM"), electrically erasable programmable read-only memory ("EEPROM"), compact disc (CD)-ROM, digital versatile disks (DVD) or other optical storage, magnetic cassettes, magnetic tape, magnetic disk storage or other magnetic storage devices, RAID storage systems, or any other tangible medium which can be used to store the desired information and which can be accessed by the processor(s) 406.

The power source(s) 410 may include one or more batteries, such as a battery pack. The power source(s) 410 may be removable and/or rechargeable. In some embodiments, the power source(s) 410 may include one or more solar panels. The communication interface(s) 412 may be configured to facilitate a wireless and/or wired connection to a network and/or to another device(s), such as a nearby computing device (e.g., a tablet or a mobile phone). An example is shown in FIG. 4 where the EMS suit 100 may be communicatively coupled to the computing device 402 via the communications interface(s) 412. For example, the processor(s) 406 may be configured to process computer-executable instructions and/or data received via the communications interface(s) 412 from the computing device 402 that cause the electrode(s) 112 to deliver an impulse(s) to one or more muscle group(s) in accordance with specified output parameters. Furthermore, adjustments to the output parameters (e.g., intensity adjustments) made by a user via the computing device 402 may be received via the communications interface(s) 412 and processed by the processor(s) 406 to adjust the output provided via the electrodes 112. For example, the multiple electrodes 112 described herein may map to different muscle groups designated by respective channels 202 of an array of channels 202. For example, a first channel 202 may be designated for a pair of electrodes 200 on the pants portion 104, a second channel 202 for a pair of electrodes 200 on the vest portion 102, a third channel 202 for a pair of electrodes 200 on an arm band 106, and so on and so forth. The electrodes 112 of the example EMS suit 100 shown in FIG. 1 may map to a total of N channels (e.g., N=13 channels), where each channel 202 controls electrical impulse delivery of a given pair of electrodes 200. The electrical impulse intensity for these respective channels 202 may be adjustable independent of the other channels 202, and each channel 202 may be independently operated (e.g., electrical impulses may be delivered via electrodes 112 positioned on the legs of the user, without eliciting muscle contraction of the user's upper body at all). Therefore, muscle groups can be isolated to contract particular targeted muscles, and the intensities of each channel 202 may be set at relative levels (e.g., less intense on the legs, more intense on the arms, etc.). Thus, relative, per-channel 202 (or per-muscle group) settings of intensity levels can be maintained in the pulse parameters 414, and the adjustments made by the user may increase or decrease at least some of these parameters 414. Furthermore, the arrangement of the electrodes 112 on the EMS suit 100 described herein allows for one-sided delivery of electrical impulses (e.g., to one side of the body or the other, relative to the midsagittal plane 304). That is, if the user has an injury on his/her right arm, or if the user is an amputee with only a left arm, the EMS suit 100 may be controlled to deliver electrical impulses to a channel 202(7) for the left arm, without delivering electrical impulses to a channel 202(8) for the right arm.

The communication interface(s) 412 may implement multiple types of wireless or radio technologies, such as a radio that is configured to operate as a Bluetooth radio (e.g., Bluetooth Low Energy (BLE) radio), a Wi-Fi radio, a cellular radio, and/or combinations thereof. Therefore, in at least some embodiments, the communication interface(s) 412 may comprise a wireless communication interface (e.g., wireless radio). It is to be appreciated that the communication interface(s) 412 may further include physical ports to facilitate a wired connection to a network, a connected peripheral device, or a plug-in network device that communicates with other wireless networks. In any case, the communications interface(s) 412 may allow for receiving commands from a nearby computing device(s) (e.g., the computing device 402) to control an aspect of output provided by the EMS suit 100. For example, a command may be received wirelessly via the communication interface(s) 412 to control the initiation of an electrical impulse(s), the cessation of an electrical impulse(s), or adjustment of an intensity of an electrical impulse(s) delivered via an electrode(s) 112 of the EMS suit 100.

Several modules such as instruction, datastores, and so forth may be stored within the memory 408 and configured to execute on the processor(s) 406. An operating system module 416 may be configured to manage hardware within and coupled to the EMS suit 100 for the benefit of other modules, for example. The memory 408 may further store pulse parameters 414 that are used to control the output of the electrodes 112. For example, an electrical impulse that is delivered via any electrode pair 200, as described herein, may include individual pulses of electrical energy. Suitable current types that can be used to deliver electrical impulses via electrodes 112 of the EMS suit 100 include, without limitation, alternating current (AC) and pulsatile (or pulsed)

current. Suitable waveforms that can be used to deliver electrical impulses via electrodes 112 of the EMS suit 100 include, without limitation, waveforms of a monophasic shape, biphasic shape, or polyphasic shape, which may be symmetrical or asymmetrical, and balanced or unbalanced. In some embodiments, electrical impulses are delivered using waveforms that are symmetrical, balanced, and biphasic. During a given pulse of electrical energy delivered via a given pair of electrodes 200 of a frame, current may flow between the electrodes 112 of the pair 200 by traveling through a portion of the user's body 302 (e.g., the muscle tissue underlying the pair of electrodes 200). In some embodiments, the processor(s) 406 of the EMS suit 100 is configured to deliver electrical impulses sequentially over multiple channels 202 to allow for serialized delivery of electrical impulses per electrode pair 200, as described herein. Accordingly, electrical impulse delivery may occur sequentially, channel-by-channel, one channel 202 after another. Pulse parameters 414 (or attributes) of electrical impulses delivered via electrodes 112 of the EMS suit 100 may include, without limitation, pulse width (or pulse duration), frequency (e.g., the number of pulses per second, measured in Hz), inter-pulse interval (e.g., the time between individual pulses, or an "OFF time"), phase duration (e.g., the duration of one phase of the pulse, or an "ON time"), interphase interval (e.g., the time between phases of a pulse), pulse intensity (amplitude), ramp up time (e.g., the time it takes for the current intensity to increase from zero to its maximum intensity), plateau time (e.g., the time during which the pulse remains at a maximum intensity), and/or ramp down time (e.g., the time it takes for the current intensity to decrease from its maximum intensity to zero). A maximum intensity (or current-cap) value to which the pulses may be adjustable may be about 90 milliamps (mA), about 100 mA, about 110 mA, or about 120 mA. The maximum intensity (or current-cap) may be based on the hardware limitation of the EMS suit 100 and/or the system 400 in which the EMS suit 100 is implemented, or the maximum intensity (or current-cap) may be implemented in software of the EMS suit 100 and/or the system 400 in which the EMS suit 100 is implemented. Pulse width may be set within a range of about 175 microseconds (μs) to about 400 μs. Frequency may be set within a range of about 80 Hz to about 120 Hz. However, these are merely exemplary values, and other pulse parameter 414 settings may be utilized.

As shown in FIG. 4, the computing device 402 may include one or more input/output (I/O) devices 418, such as the controls (e.g., joysticks, trackpads, triggers, depressible buttons, etc.), potentially any other type of input or output devices. For example, the I/O devices 418 may include one or more microphones to receive audio input, such as user voice input. In some implementations, one or more cameras or other types of sensors may function as input devices to receive gestural input, such as motion of the computing device 402. In some embodiments, additional input devices may be provided in the form of a keyboard, keypad, mouse, touch screen, joystick, control buttons, motion sensors, accelerometer(s), gyroscope(s), inertial measurement unit(s) (IMU(s)), and the like. The input device(s) may further include control mechanisms, such as basic volume control button(s) for increasing/decreasing volume, as well as power and reset buttons.

The output devices, meanwhile, may include a display(s), a light element (e.g., LED), a vibrator to create haptic sensations, a speaker(s) (e.g., headphones), and/or the like. While a few examples have been provided, the computing device 402 may additionally or alternatively comprise any other type of output device. In some instances, output by the one or more output devices may be based on input received by one or more of the input devices. For example, actuation of a control or the touchscreen may result in the output of a haptic response by a vibrator located adjacent (e.g., underneath) the control, the touchscreen, or at any other location.

The computing device 402 is shown as including one or more processors 420, memory 422 (or non-transitory computer-readable media 422), and a communications interface(s) 424. These components may be implemented similarly to the processor(s) 406, memory 408, and communication interface(s) 412 described with reference to the EMS suit 100, and, as such, details of these components will not be explained again for the sake of brevity, as the description of the processor(s) 406, memory 408, and communication interface(s) 412 may be referenced herein to understand example implementations of the processor(s) 420, memory 422, and communication interface(s) 424. Several modules such as instruction, datastores, and so forth may be stored within the memory 422 and configured to execute on the processor(s) 420. A few example functional modules are shown as stored in the memory 422 and executed on the processor(s) 420, although the same functionality may alternatively be implemented in hardware, firmware, or as a SOC.

An operating system module 426 may be configured to manage hardware within and coupled to the computing device 402 for the benefit of other modules. In addition, the memory 422 may store a client application 428, which may represent an executable application (e.g., code, computer-executable instructions, etc.) that is configured to decode media data and/or command data, to playback the media data (e.g., a video of an instructor performing a workout session), to process command data, to generate and send commands to the EMS suit 100 based at least in part on the command data, and/or to cause presentation of graphical overlays atop media content based at least in part on the command data. The client application 428 may provide a user interface for a user to initiate playback of media data (e.g., a video file(s)) representing a workout session conducted by an instructor, for example. The user can provide user input (e.g., select a button, such as a physical button on the device or a soft button (e.g., a "play" icon) on a touch screen), issue a voice command, etc.) to start playback of the media data or to start the workout session when the user is ready to start, and/or the user may adjust the output of the EMS suit 100 via a user interface of the computing device 402 (e.g., via a touchscreen). The memory 422 may further include a data store, which may store one or more user profiles 430, such as a user profile 430 of a user who has logged into the client application 428 in the past, as well as media data and/or command data generated by the computing device 402 or received (e.g., downloaded) from a remote system over a wide area network (e.g., the Internet).

It is to be appreciated that some or all of the components shown in FIG. 4, with the exception of the electrodes 112, may be provided in an impulse pack situated in or on the EMS suit 100. Furthermore, the electrodes 112 may be coupled to the processor(s) 406 via electrical wires (or wirelessly), and the EMS suit 100 may be communicatively coupled to the processor(s) 420 of the computing device 402. Furthermore, a layer of base material (e.g., an undergarment) may be worn between the electrode(s) 112 and the skin of the user. In some embodiments, gel and/or water and/or similar materials may be interposed between the electrode(s) 112 and the base layer of material to improve electrical conductivity.

The processes described herein are illustrated as a collection of blocks in a logical flow graph, which represent a sequence of operations that can be implemented in hardware, software, or a combination thereof. In the context of software, the blocks represent computer-executable instructions that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the processes.

Figure 5:
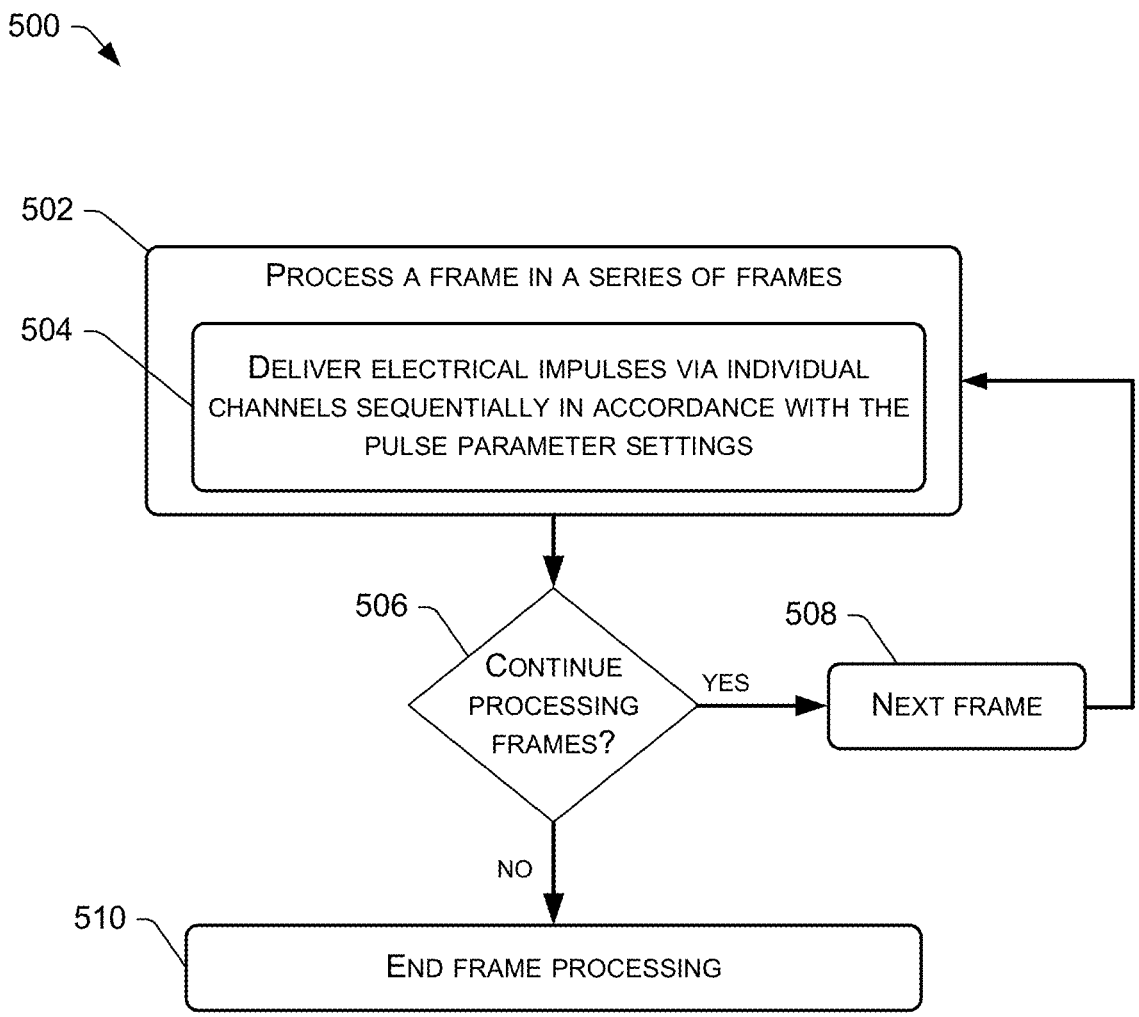
FIG. 5 is a flow diagram of an example process for controlling an EMS suit to deliver electrical impulses via electrodes arranged in a manner to prevent transthoracic electrical current, in accordance with embodiments disclosed herein.

FIG. 5 is a flow diagram of an example process 500 for controlling an EMS suit 100 to deliver electrical impulses via electrodes 112 arranged in a manner to prevent transthoracic electrical current, in accordance with embodiments disclosed herein. For discussion purposes, the process 500 is described with reference to the previous figures.

At 502, a processor(s) (e.g., the processor(s) 406 and/or the processor(s) 420) may process a frame in a series of frames. The series of frames, when processed, may cause electrical impulses to be delivered via electrodes 112 of the EMS suit 100 in order to elicit muscle contraction of a user wearing the EMS suit 100. A frame rate at which the series of frames may be processed can be any suitable frame rate, such as a frame rate within a range of about 1-120 Hz. The series of frames may be processed during a workout session while a user is using the EMS suit 100. Block 504 may represent a sub-operation(s) of block 502 during the processing of a frame.

At 504, the processor(s) (e.g., the processor(s) 406 and/or the processor(s) 420) may cause circuitry of the EMS suit 100 to deliver electrical impulses to individual channels 202 of multiple (N) channels 202 sequentially (or in the sequence), one channel 202 after another, and in accordance with the pulse parameter 414 settings (e.g., intensity (amplitude), pulse width, etc.). For example, a first electrical impulse may be delivered via the first pair of electrodes 200(1) corresponding to a first channel 202(1), followed by a second electrical impulse delivered via the second pair of electrodes 200(2) corresponding to a second channel 202(2), and so on and so forth for any suitable number of N channels 202 and any suitable number of P electrodes 112. As described herein, due to the arrangement of the electrodes 112 in a region of the thoracic cavity of the user, transthoracic flow of electrical current is prevented.

At block 506, the processor(s) (e.g., the processor(s) 406 and/or the processor(s) 420) may determine whether to continue processing frames of the series of frames. If a next frame is to be processed, the process 500 may follow the "YES" route from block 506 to block 508 by transitioning to the next frame, and by processing the next frame in the series of frames at block 502. If a next frame is not to be processed, the process 500 may end frame processing at block 510 by following the "NO" route from block 506 to block 510. For example, if an end of a workout session has been reached, the processor(s) (e.g., the processor(s) 406 and/or the processor(s) 420) may determine to end frame processing at block 510 so that the user can remove the EMS suit 100 from his/her body 302.

Figure 6A:
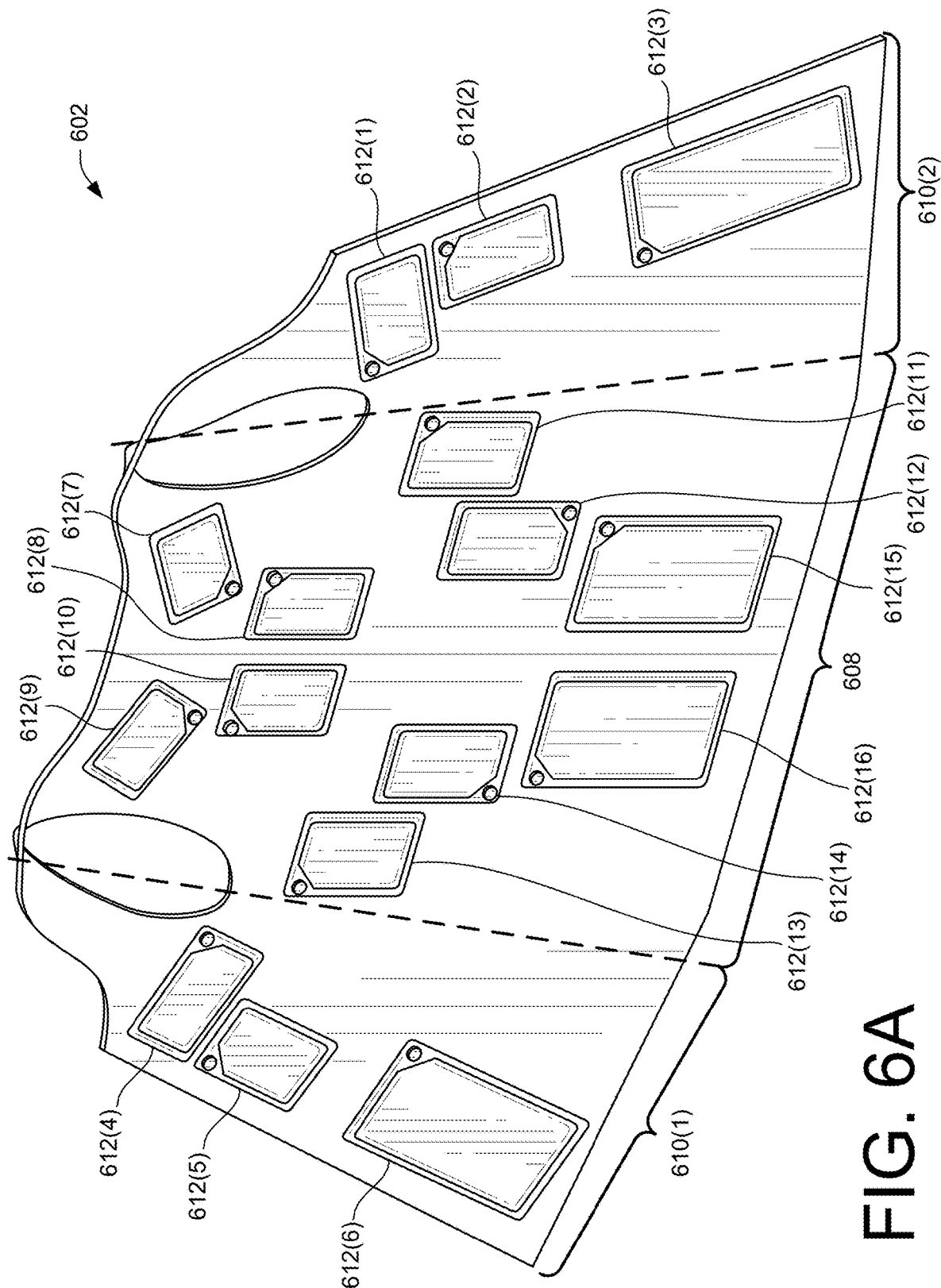
FIG. 6A is a perspective view of an example vest portion of an EMS suit, the vest portion shown in an opened configuration, and the vest portion having an arrangement of electrodes that prevents transthoracic electrical current, according to embodiments described herein.
Figure 6B:
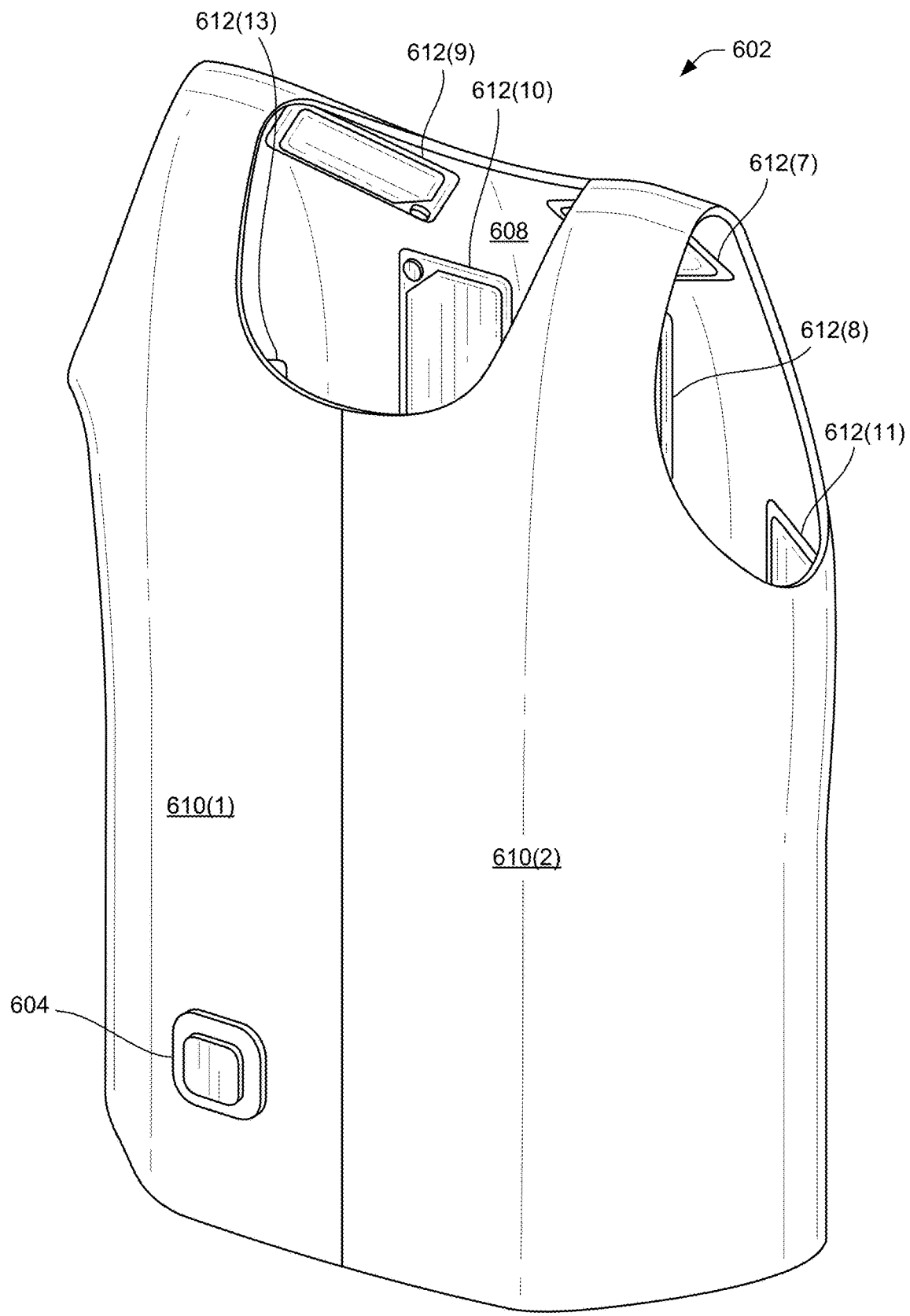
FIG. 6B is a perspective view of the example vest portion of the EMS suit of FIG. 6A, with the vest portion in a closed configuration, according to embodiments described herein.

FIG. 6A is a perspective view of an example vest portion 602 of an EMS suit 100, the vest portion 602 shown in an opened configuration, and the vest portion 602 having an arrangement of electrodes 612 that prevents transthoracic electrical current, according to embodiments described herein. FIG. 6B is a perspective view of the example vest portion 602 of the EMS suit 100 of FIG. 6A, with the vest portion 602 in a closed configuration, according to embodiments described herein. Similarly to the vest portion 102 described with reference to at least FIG. 1, the vest portion 602 of FIG. 6A is to be worn on an upper trunk of a user's body 302. Unless otherwise stated herein to the contrary, the vest portion 602 may include any components or features described with reference to the vest portion 102 shown in at least FIG. 1.

The vest portion 602 may comprise a back portion 608, a right front portion 610(1), and a left front portion 610(2). When the vest portion 602 is worn by a user, the back portion 608 covers at least a portion of the user's back (e.g., the back of the upper trunk of the body), the right front portion 610(1) covers at least a portion of the user's right thorax and abdomen (e.g., the front-right half of the upper trunk of the body), and the left front portion 610(2) covers at least a portion of the user's left thorax and abdomen (e.g., the front-left half of the upper trunk of the body).

One exemplary difference between the vest portion 102 shown in FIG. 1 and the vest portion 602 shown in FIGS. 6A and 6B is that the vest portion 602 can either omit or internalize components shown in FIG. 1, such as the straps 114 that are shown in FIG. 1. In other words, the vest portion 102 shown in FIG. 1 includes separate portions 108, 110(1), and 110(2) that are not contiguous. These separate portions 108, 110(1), and 110(2) are instead connected, or connectable, via the straps 114 shown in FIG. 1. By contrast, the portions 608, 610(1), and 610(2) of the vest portion 602 shown in FIGS. 6A and 6B are depicted as being contiguous with each other. Accordingly, FIG. 6A delineates the portions 608, 610(1), and 610(2) using imaginary dashed lines. By fabricating the vest portion 602 to have contiguous portions 608, 610(1), and 610(2) (e.g., by making the vest portion 602 out of a substantially unitary piece(s) of fabric), various components of the vest portion 602 can be internalized within the fabric of the vest portion 602. For example, the wiring that connects the electrodes 612 to other electronics that are either a part of, or connected to, the vest portion 602 can be internalized within the fabric. In the example of FIG. 6B, an external connector 604 is shown on an outer surface of the right front portion 610 of the vest portion 602. This external connector 604 may be configured to connect to an impulse pack, the impulse pack configured to control the delivery of the electrical impulses via the electrodes 612, as described herein. The external connector 604 may also be connected to the wiring that is internal to the fabric of the vest portion 602, and the internal wiring may be connected to each of the electrodes 612.

FIG. 6A depicts multiple electrodes 612 on the vest portion 602, as an illustrative example. The electrodes 612 may be affixed to the vest portion 602 in any suitable manner. For example, the electrodes 612 can be adhered or bonded to the vest portion 602 using an adhesive (e.g., glue), sewn into pockets or pouches of vest portion 602, enclosed using rivets or other fastener mechanisms, etc. The electrodes 612 can be permanently affixed to the vest portion 602 (i.e., the user may be unable to remove, replace, and/or move the electrodes 612 without tearing apart the vest portion 602 in a destructive manner). In some embodiments, however, the electrodes 612 may be removable (e.g., by housing the electrodes 612 within pockets or pouches that are openable (e.g., pouches with zippers or snap buttons to open and close the pouch for insertion/removal of the electrodes 612). In some embodiments, an individual electrode 612 and at least some wiring connected thereto may be secured within the vest portion 602 using a rivet or a similar fastener during fabrication of the vest portion 602.

By fabricating the vest portion 602 in the manner shown in FIGS. 6A and 6B (e.g., with contiguous portions 608, 610(1), and 610(2)), the vest portion 602 may have an aesthetically pleasing (e.g., sleek) appearance, and there may be little-to-no exposed wires to avoid damaging the suit (e.g., exposed wires can snag on things). The construction of the vest portion 602 shown in FIGS. 6A and 6B also makes the vest portion 602 easy to clean. For example, a user may place the vest portion 602 in a washing machine to clean it. A washable vest portion 602 may include an external connector 604 that is water tight and that prevents the ingress of water, among other elements, via the connector 604. The electrodes 612 may also be affixed to the vest portion 602 using a water-tight seal, thereby preventing the ingress of water, among other elements, via the electrodes 612.

As shown at least in FIG. 6A, the vest portion 602 includes electrodes 612(1)-(16). The details of these electrodes 612(1)-(16) will not be described further for the sake of brevity, as reference can be made to the electrodes 112(1)-(16) for an understanding of the electrodes 612(1)-(16), including an understanding of how the electrodes 612 are positioned on the user's body 302 when the vest portion 602 is worn by a user, and how the electrodes 612 can function during operation of the EMS suit 100. Like the electrodes 112(1)-(16), the electrodes 612(1)-(16) can be arranged in pairs that operate as described herein with reference to the electrodes 112(1)-(16) to prevent transthoracic electrical current during operation of the EMS suit 100.

Although pairs of electrodes 112/612 are described herein as a first pair 200(1), a second pair 200(2), a third pair 200(3), and so on, it is to be appreciated that the particular number attributed to the individual pairs 200 is interchangeable. That is, the recitation of a "first" pair of electrodes, as used herein, can mean any pair of electrodes 200 described herein and shown in the Figures. The use of "first," "second," "third," etc., in this context, is meant to distinguish or disambiguate one pair of electrodes from another.

Unless otherwise indicated, all numbers expressing quantities used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

The environment and individual elements described herein may of course include many other logical, programmatic, and physical components, of which those shown in the accompanying figures are merely examples that are related to the discussion herein.

Other architectures may be used to implement the described functionality, and are intended to be within the scope of this disclosure. Furthermore, although specific distributions of responsibilities are defined above for purposes of discussion, the various functions and responsibilities might be distributed and divided in different ways, depending on circumstances.

Furthermore, although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

Although the subject matter has been described in language specific to structural features and/or methodological acts, it is to be understood that the subject matter defined in the appended claims is not necessarily limited to the specific features or acts described. Rather, the specific features and acts are disclosed as illustrative forms of implementing the claims.

What is claimed is:

1. An electrical muscle stimulation (EMS) suit comprising:
   a vest portion comprising:
      a left front portion comprising a first pair of electrodes corresponding to a first channel of multiple channels, the first pair of electrodes disposed on an inner surface of the vest portion, positioned within a top half of the left front portion, and configured to be disposed on one or more left pectoral muscles of a body when the body is wearing the EMS suit;
      a right front portion comprising a second pair of electrodes corresponding to a second channel of the multiple channels, the second pair of electrodes disposed on the inner surface of the vest portion, positioned within a top half of the right front portion, and configured to be disposed on one or more right pectoral muscles of the body when the body is wearing the EMS suit;
      a third pair of electrodes corresponding to a third channel of the multiple channels, the third pair of electrodes disposed on the inner surface of the vest portion, wherein:
         a first electrode of the third pair of electrodes is positioned within a bottom half of the left front portion and is configured to be disposed on one or more left abdominal muscles of the body when the body is wearing the EMS suit; and
         a second electrode of the third pair of electrodes is positioned within a bottom half of the right front portion and is configured to be disposed on one or more right abdominal muscles of the body when the body is wearing the EMS suit;
      a back portion comprising:
         a fourth pair of electrodes corresponding to a fourth channel of the multiple channels, the fourth pair of electrodes disposed on the inner surface of the vest portion, positioned within a left half of the back portion, and configured to be disposed on one or more left upper back muscles of the body when the body is wearing the EMS suit;

a fifth pair of electrodes corresponding to a fifth channel of the multiple channels, the fifth pair of electrodes disposed on the inner surface of the vest portion, positioned within a right half of the back portion, and configured to be disposed on one or more right upper back muscles of the body when the body is wearing the EMS suit;

a sixth pair of electrodes corresponding to a sixth channel of the multiple channels, the sixth pair of electrodes disposed on the inner surface of the vest portion, positioned within the left half of the back portion, positioned below the fourth pair of electrodes, and configured to be disposed on one or more left middle back muscles of the body when the body is wearing the EMS suit;

a seventh pair of electrodes corresponding to a seventh channel of the multiple channels, the seventh pair of electrodes disposed on the inner surface of the vest portion, positioned within the right half of the back portion, positioned below the fifth pair of electrodes, and configured to be disposed on one or more right middle back muscles of the body when the body is wearing the EMS suit; and an eighth pair of electrodes corresponding to an eighth channel of the multiple channels, the eighth pair of electrodes disposed on the inner surface of the vest portion, wherein:
  a first electrode of the eighth pair of electrodes is positioned within the left half of the back portion, is positioned below the sixth pair of electrodes, and is configured to be disposed on one or more left lower back muscles of the body when the body is wearing the EMS suit; and
  a second electrode of the eighth pair of electrodes is positioned within the right half of the back portion, is positioned below the seventh pair of electrodes, and is configured to be disposed on one or more right lower back muscles of the body when the body is wearing the EMS suit;

a first arm band comprising a ninth pair of electrodes corresponding to a ninth channel of the multiple channels, the ninth pair of electrodes configured to be disposed on one or more left upper arm muscles of the body when the body is wearing the EMS suit;

a second arm band comprising a tenth pair of electrodes corresponding to a tenth channel of the multiple channels, the tenth pair of electrodes configured to be disposed on one or more right upper arm muscles of the body when the body is wearing the EMS suit;

a processor; and memory storing:
  pulse parameter settings comprising a frequency parameter set within a range of about 80 Hertz (Hz) to about 120 Hz; and
  computer-executable instructions that, when executed by the processor, cause electrical impulses to be delivered via the first pair of electrodes, the second pair of electrodes, the third pair of electrodes, the fourth pair of electrodes, the fifth pair of electrodes, the sixth pair of electrodes, the seventh pair of electrodes, the eighth pair of electrodes, the ninth pair of electrodes, and the tenth pair of electrodes in accordance with the pulse parameter settings.

2. The EMS suit of claim 1, wherein, during operation of the EMS suit, electrical current resulting from first electrical impulses of the electrical impulses delivered via the first pair of electrodes and second electrical impulses of the electrical impulses delivered via the second pair of electrodes does not cross a midsagittal plane of the body when the body is wearing the EMS suit.

3. The EMS suit of claim 1, wherein, during operation of the EMS suit, electrical current resulting from first electrical impulses of the electrical impulses delivered via the first pair of electrodes, second electrical impulses of the electrical impulses delivered via the second pair of electrodes, third electrical impulses delivered via the fourth pair of electrodes, and fourth electrical impulses delivered via the fifth pair of electrodes does not cross:
  a midsagittal plane of the body when the body is wearing the EMS suit; and
  a frontal plane of the body when the body is wearing the EMS suit.

4. The EMS suit of claim 1, further comprising a pants portion comprising:
  an eleventh pair of electrodes corresponding to an eleventh channel of the multiple channels, the eleventh pair of electrodes configured to be disposed on one or more glute muscles of the body when the body is wearing the EMS suit;
  a twelfth pair of electrodes corresponding to a twelfth channel of the multiple channels, the twelfth pair of electrodes configured to be disposed on one or more hamstring muscles of the body when the body is wearing the EMS suit; and
  a thirteenth pair of electrodes corresponding to a thirteenth channel of the multiple channels, the thirteenth pair of electrodes configured to be disposed on one or more quadricep muscles of the body when the body is wearing the EMS suit.

5. The EMS suit of claim 1, wherein the electrical impulses are sequentially delivered via the multiple channels.

6. The EMS suit of claim 1, wherein the pulse parameter settings further comprise a pulse width parameter set within a range of about 175 microseconds (µs) to about 400 µs.

7. The EMS suit of claim 1, further comprising an external connector disposed on an outer surface of the vest portion and configured to connect to an impulse pack.

8. The EMS suit of claim 1, wherein each electrode of the first pair of electrodes, the second pair of electrodes, the third pair of electrodes, the fourth pair of electrodes, the fifth pair of electrodes, the sixth pair of electrodes, the seventh pair of electrodes, the eighth pair of electrodes, the ninth pair of electrodes, and the tenth pair of electrodes has a rectangular shape.

* * * * *